United States Patent
Lian et al.

(10) Patent No.: US 8,315,694 B2
(45) Date of Patent: Nov. 20, 2012

(54) METHOD AND APPARATUS FOR ECTOPIC BEAT DETECTION

(75) Inventors: Jie Lian, Beaverton, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 879 days.

(21) Appl. No.: 12/252,529

(22) Filed: Oct. 16, 2008

(65) Prior Publication Data

US 2010/0099995 A1    Apr. 22, 2010

(51) Int. Cl.
*A61B 5/04*    (2006.01)
(52) U.S. Cl. ........................................ 600/509
(58) Field of Classification Search .................. 600/509
See application file for complete search history.

(56) References Cited

U.S. PATENT DOCUMENTS

| | | | | |
|---|---|---|---|---|
| 5,817,133 A * | 10/1998 | Houben | ............................. | 607/9 |
| 5,891,048 A | 4/1999 | Nigam | | |
| 6,470,215 B1 | 10/2002 | Kraus | | |
| 6,574,509 B1 | 6/2003 | Kraus | | |
| 6,622,043 B1 | 9/2003 | Kraus | | |
| 7,187,965 B2 * | 3/2007 | Bischoff et al. | ............... | 600/515 |
| 7,228,173 B2 * | 6/2007 | Cazares | .......................... | 607/14 |
| 2004/0158295 A1 * | 8/2004 | Dyjach et al. | .................. | 607/25 |
| 2005/0234361 A1 * | 10/2005 | Holland | ........................ | 600/510 |
| 2007/0265667 A1 | 11/2007 | Muessig | | |

* cited by examiner

*Primary Examiner* — Niketa Patel
*Assistant Examiner* — Philip Edwards
(74) *Attorney, Agent, or Firm* — ARC IP Law, PC; Joseph J. Mayo

(57) ABSTRACT

Heart monitor for detecting ectopic beats in an input electrocardiogram signal that includes an electrocardiogram signal input and a morphological signal analyzer connected to the electrocardiogram signal input, the analyzer being adapted to generate a first time series of values representing the input electrocardiogram signal, a second signal analyzer adapted to generate generating a modified time series of values representing a trend of values of the first time series and a comparison stage being adapted to compare the first time series with the modified time series to thus detect ectopic beats. The invention further relates to a method for detecting ectopic beats in an input electrocardiogram signal that includes obtaining an electrocardiogram signal, generating from the electrocardiogram signal a first time series of values representing the input electrocardiogram signal, generating a modified time series of values representing a trend of values of the first time series and comparing the first time series with the modified time series to thus detect ectopic beats.

19 Claims, 22 Drawing Sheets

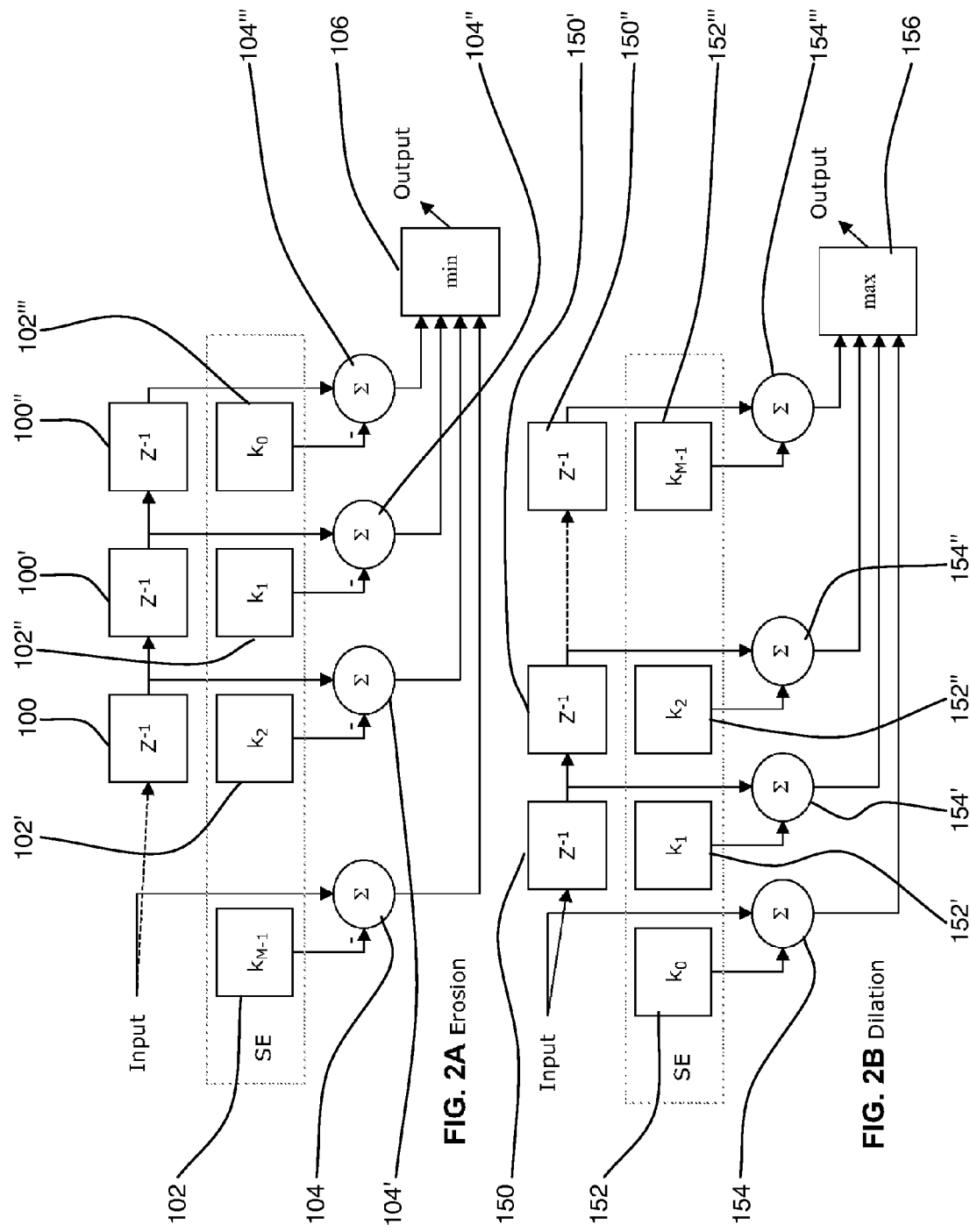
FIG. 2A Erosion
FIG. 2B Dilation

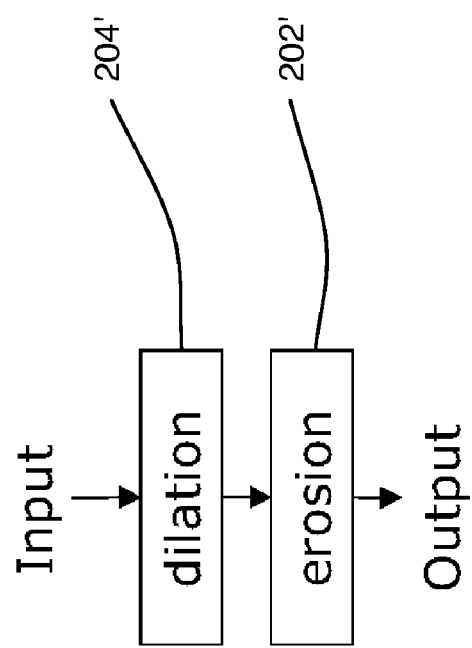
FIG. 3B Closing
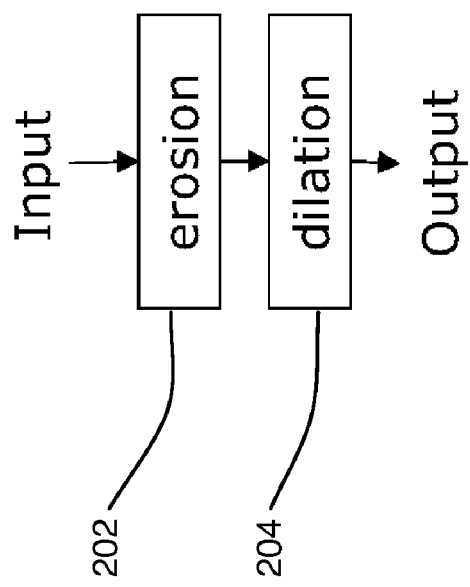
FIG. 3A Opening

METHOD AND APPARATUS FOR ECTOPIC BEAT DETECTION

BACKGROUND OF THE INVENTION

1. Field of the Invention

The present invention generally relates to medical devices that measure cardiac inter-beat intervals and analyze the cardiac inter-beat intervals. More particularly, the present invention relates to a method and apparatus for accurate detection of ectopic beats, robust removal of short and long cardiac inter-beat intervals that are related to ectopic beats, and construction of artifact-free cardiac inter-beat intervals.

2. Description of the Related Art

The variation of cardiac inter-beat (e.g., PP, RR) intervals results from both rhythmic activity of the heart electrical source and the dynamic properties of the cardiac conduction pathway, both of which are under autonomic control. In normal sinus rhythm, the RR intervals are known to fluctuate at various time scales, a phenomenon known as heart rate variability (HRV), which has been extensively investigated to probe the autonomic nervous activity. On the other hand, structural or functional abnormalities of the cardiac electrical conduction system can lead to cardiac arrhythmias.

The RR interval is a preferred choice to represent cardiac inter-beat interval due to easy acquisition of the electrocardiogram (ECG) signals, and the prominent QRS complexes present in these signals. The RR intervals not only can be easily measured from the surface ECG, but also can be measured from the subcutaneous ECG that is recorded by placing electrodes under the skin, or from the intracardiac electrogram (IEGM) that is recorded by inserting electrodes into the heart. Alternatively, the cardiac inter-beat intervals can also be obtained from other types of biosignals that are known to show the same rhythmic variation as the cardiac beats, including but not limited to, the blood pressure signal, the transthoracic impedance signal, the pulse oximeter signal, finger plethysmography signal, etc.

Abnormal cardiac intervals are usually evidenced by abrupt increase or decrease of the RR interval (or heart rate). One typical type of abnormal cardiac interval is caused by ectopic beat (EB) of either atrial or ventricular origin, characterized by abrupt shortening of the RR interval as compared to the preceding RR intervals. Another typical type of abnormal cardiac interval is the long pause after the Ectopic Beat. In fact, the short Ectopic Beat interval and the long post-Ectopic Beat pause often occur in tandem, characterized by a pair of short-long RR intervals in the RR interval tachogram. The short-long RR intervals can also repeat, resulting in the so-called bigeminy rhythm with alternating short and long RR intervals. Yet another type of abnormal cardiac interval is caused by consecutive Ectopic Beats, for example, the duplets, the triplets, or non-sustained ventricular tachycardia (NSVT), characterized by multiple consecutive short RR intervals in the tachogram. Yet another type of abnormal cardiac interval is caused by sudden drop of heart rate, for example, in patients with sick sinus syndrome or transient AV block, evidenced by abrupt increase of the RR intervals in the tachogram. Yet abnormal cardiac intervals can also be caused by transient sensing problems, for example, under-sensing of the R wave (resulting in abrupt increase of RR interval), over-sensing of the T wave (resulting in abrupt decrease of RR interval), or sensing of exogenous noise.

Detection of abnormal cardiac interval is a crucial step in time series analysis of RR intervals. For example, in Holter ECG analysis, daily Ectopic Beat counter (or Ectopic Beat frequency) is a simple yet important parameter for cardiac arrhythmia risk stratification. In another example, calculation of HRV parameters involves only normal cardiac inter-beat intervals, thus abnormal cardiac intervals must be removed prior to HRV evaluation. In addition, the heart rate turbulence (HRT) quantifies the short-term fluctuation in sinus cycle length that follows a ventricular Ectopic Beat, and has been shown to be a strong predictor of mortality and sudden cardiac death following myocardial infarction. Furthermore, the Ectopic Beat-free RR intervals can also be used to assess the baseline heart rate, its trend, and its circadian pattern.

Numerous techniques have been developed for automatic detection of Ectopic Beats from the ECG signals. One typical approach for Ectopic Beat detection is by means of morphological analysis of the ECG signals, based on the observation that ventricular Ectopic Beats typically have different QRS morphology than the normally conducted QRS morphology. However, this approach has several limitations. First, it cannot be used for Ectopic Beat detection from RR intervals only because it requires ECG morphological information. Second, depending on the source of the Ectopic Beats, the QRS morphology of the Ectopic Beats may not be necessarily different than that of the normally conducted QRS complexes. Third, morphology-based Ectopic Beat detection could not be applied to identify other types of abnormal cardiac cycles, for example, long ventricular pauses due to transient AV block or sudden drop of sinus rate.

Alternatively, Ectopic Beat detection can be achieved by analyzing time series of cardiac intervals. In implantable cardiac pacemakers and defibrillators, the Ectopic Beat detection is usually achieved by analyzing the atrial-ventricular relationship when sensing electrodes are placed in both atrium (e.g., RA) and ventricle (e.g., RV or LV). For example, a ventricular sense (VS) outside the ventricular refractory period is usually classified as a normal ventricular depolarization if it is preceded by an atrial event (atrial sense, or atrial pace) within a predefined time interval, or a ventricular Ectopic Beat otherwise.

In single chamber pacemakers or defibrillators, the Ectopic Beat detection becomes more challenging since atrial-ventricular association or dissociation could not be assessed. Conventionally, the ventricular Ectopic Beat detection is usually achieved by calculating the ventricular prematurity index by comparing each RR interval with the mean or median of previous several RR intervals. Similarly, the atrial Ectopic Beat detection can be achieved by calculating the atrial prematurity index by comparing each PP interval with the mean or median of previous several PP intervals.

Several other methods have been proposed for Ectopic Beat detection from time series of RR intervals. Most of these methods involve calculation of mean RR interval (or heart rate), standard deviation of RR intervals (or heart rate), and beat-to-beat difference of RR intervals (or heart rate). Other methods include polynomial fitting of the RR intervals, and median filter of the RR intervals. Based on our experience, none of these methods has satisfactory performance in terms of sensitivity and specificity of Ectopic Beat detection.

Morphological operators have been widely used in 2D image processing for noise removal, and have shown to have better edge preservation performance than other linear or nonlinear filters. The morphological operators have very high computation efficiency, and can be implemented in hardware platform, thus they are particularly suitable for application in low-power devices.

However, the application of morphological operators in 1D signal processing, in particular the ECG signal processing, has been limited. Morphological operators were used to implement a peak-valley extractor for QRS complex detection in ECG signals. Another morphological approach was developed to detect QRS complexes and remove baseline wander in neonatal ECG signals. Such approach was disclosed in U.S. Pat. No. 5,817,133 issued to Houben, for discriminating P waves from far-field R waves in an implantable pacemaker.

BRIEF SUMMARY OF THE INVENTION

It is an object of the invention to provide another method and apparatus for Ectopic Beat detection.

According to a first aspect of this invention, this object is achieved by a heart monitor for detecting ectopic beats in an input electrocardiogram signal, said heart monitor comprising
- an electrocardiogram signal input and
- a (first) signal analyzer connected to said electrocardiogram signal input, said signal analyzer being adapted to generate a first time series of values representing said input electrocardiogram signal,
- a second signal analyzer adapted to generate a modified time series of values representing a trend of values of said first time series and
- a comparison stage being adapted to compare said first time series with said modified time series to thus detect ectopic beats.

The first time series of values representing said input electrocardiogram signal can e.g. be a time series of measured RR-intervals or time series of QRS metrics other than RR intervals or a combination of both.

Preferred embodiments include:

A heart monitor, wherein the signal analyzer is adapted to generate a time series of values representing QRS metrics (that is the first time series), wherein each value of the time series represents at least one of the QRS metrics, such as the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex. The second signal analyzer is preferably adapted to apply morphological operators to the time series of QRS metrics and to remove abnormal QRS metrics from said time series of QRS metrics to thus derive said modified time series representing a trend of said QRS metrics.

A heart monitor, wherein the signal analyzer is adapted to generate a first time series of values representing each duration of a respectively measured RR interval, and wherein said second signal analyzer is adapted to apply morphological operators to said first time series of measured RR-intervals and to remove abnormal RR intervals from said first time series of measured RR intervals to thus derive said modified time series of RR-intervals representing a trend of RR intervals.

Typically, the comparison stage is adapted to subtract said first time series from said modified time series and to thus generate difference signal values and detect abnormal RR intervals or QRS metrics by comparing said difference signal values to at least one threshold value.

Alternatively, the comparison stage can be adapted to generate a series of ratio values by dividing each value of said first time series by its associated value of said modified time series and to compare each ratio value thus derived with at least one threshold value.

Preferably, the comparison stage can be adapted to generate both the difference signal values and the ratio values and to compare each difference signal value to at least one threshold value and to compare each ratio value with at least one threshold value.

Preferably, the morphological signal analyzer is adapted to generate said modified time series by applying both, an erosion operator and a dilation operator to said first time series to thus obtain said modified time series of values representing a trend of values of said first time series. The erosion operator and the dilation operator both are morphological operators.

According to a second aspect of this invention, the object of the invention is achieved by a method for detecting ectopic beats in an input electrocardiogram signal, said heart monitor comprising the steps of
- Obtaining an electrocardiogram signal
- Generating from said electrocardiogram signal a first time series of values representing said input electrocardiogram signal,
- Generating a modified time series of values representing a trend of values of said first time series and
- Comparing said first time series with said modified time series to thus detect ectopic beats.

The first time series of values representing said input electrocardiogram signal can e.g. be a time series of measured RR-intervals or time series of QRS metrics other than RR intervals or a combination of both.

Preferred methods include:

A step of generating a first time series comprises generating a time series of values representing QRS metrics (as the first time series), wherein each value of said modified time series represents at least one of the QRS metrics, such as the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex. The method preferably further includes a step of generating a modified time series comprises applying morphological operators to the time series of QRS metrics and removing abnormal QRS metrics from said time series of QRS metrics to thus derive said modified time series representing a trend of said QRS metrics.

Alternatively, the step of generating a first time series comprises generating a time series of values representing each duration of a respectively measured RR interval, and the step of generating a modified time series comprises applying morphological operators to said first time series of measured RR-intervals and removing abnormal RR intervals from said first time series of measured RR intervals to thus derive said modified time series of RR-intervals representing a trend of RR intervals.

Typically, the step of comparing the first time series with the modified time series comprises subtracting said first time series from said modified time series and to thus generate difference signal values and detecting abnormal RR intervals or QRS metrics by comparing said difference signal values to at least one threshold value.

Alternatively, the step of comparing said first time series with said modified time series may comprise generating a series of ratio values by dividing each value of said first time series by its associated value of said modified time series and comparing each ratio value thus derived with at least one threshold value.

Preferably, the step of comparing the first time series with the modified time series comprises generating both the difference signal values and the ratio values and to compare each difference signal value to at least one threshold value and to compare each ratio value with at least one threshold value.

It is further preferred, that step of generating a modified time series comprises applying both, an erosion operator and a dilation operator to said first time series to thus obtain said modified time series of values representing a trend of values of said first time series. The erosion operator and a dilation operator are both morphological operators.

The step of generating a modified time series may further comprise applying an erosion operator followed by a dilation operator that together form an opening operator to suppress peaks in the first time series.

Likewise, the step of generating a modified time series may further comprise applying a dilation operator followed by an erosion operator that together form a closing operator to suppress pits in the first time series.

According to this invention, a first morphological filter forming the second signal analyzer is applied to the RR intervals to remove abrupt short and abrupt long RR intervals, and obtain Ectopic Beat-free RR intervals. The filtered out abrupt short and abrupt long RR intervals are compared to the Ectopic Beat-free RR intervals to identify the Ectopic Beat cycles.

According to another embodiment of the present invention, the Ectopic Beat detection is achieved by applying morphological operators to time series of QRS metrics (other than RR intervals) measured from the ECG signals. Preferably, the QRS metrics measures the morphology of the QRS complex, including but are not limited to, the peak amplitude, the width, the absolute area, the positive and negative slopes, etc. Alternatively, the QRS metrics measures the frequency content of the QRS complex.

Also according to a preferred embodiment of this invention, a second morphological filter forming a third signal analyzer is applied to the Ectopic Beat-free RR intervals to further detect multiple cycles of consecutive short RR intervals (e.g., non-sustained ventricular tachycardia) or multiple cycles of consecutive long RR intervals (e.g., paroxysmal sinus bradycardia).

The filtered RR intervals are used to evaluate the heart rate trend, and heart rate variability. The detected Ectopic Beats are further used for arrhythmia risk stratification, for example, to calculate the Ectopic Beat statistics and post-Ectopic Beat heart rate turbulence.

The present invention provides a novel means to detect Ectopic Beat cycles, to remove short and long RR intervals induced by Ectopic Beat, to detect non-sustained short or long RR intervals, and to obtain Ectopic Beat-free RR intervals. Compared to other methods, the morphological filter has better performance in Ectopic Beat detection in terms of accuracy and computation complexity.

The details of the invention can be understood from the following drawings and the corresponding text descriptions.

BRIEF DESCRIPTION OF THE DRAWINGS

The above and other aspects, features and advantages of the present invention will be more apparent from the following more particular description thereof, presented in conjunction with the following drawings wherein:

FIG. 2A shows the circuit block diagram for implementing the erosion operator, and FIG. 2B shows the circuit block diagram for implementing of the dilation operator.

FIG. 3A shows the block diagram of the opening operation, and

FIG. 3B shows the block diagram the closing operation.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Embodiments of the invention provide a method for automatic detection of abnormal cardiac intervals, including but are not limited to Ectopic Beats, by means of cardiac inter-beat interval analysis. The cardiac inter-beat intervals are preferably the RR intervals that are measured from the surface ECG signals (e.g., by Holter monitoring), or from the subcutaneous ECG signals (e.g., by implantable subcutaneous ECG monitoring), or from the intracardiac electrogram (e.g., by implantable pacemakers or defibrillators). Alternatively, the cardiac inter-beat intervals can also be obtained from other types of biosignals that are known to show the same rhythmic variation as the cardiac beats, including but not limited to, the blood pressure signal, the transthoracic impedance signal, the pulse oximeter signal, finger plethysmography signal, etc. In the following descriptions, we use subcutaneous ECG as an example to illustrate the concept of morphological filtering of RR intervals for detection of abnormal cardiac intervals.

Figure 1:
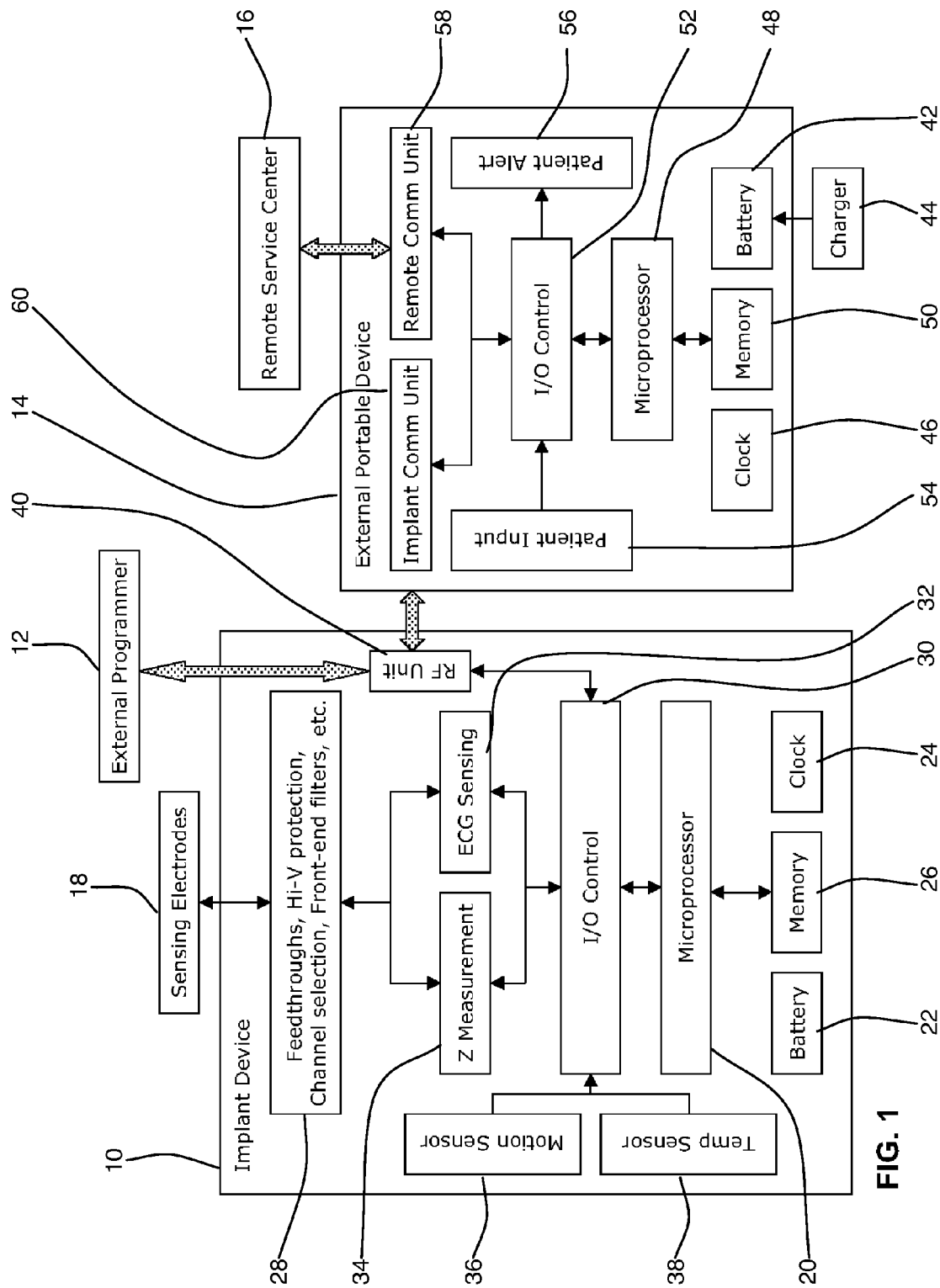
FIG. 1 shows a block diagram of an implantable device for subcutaneous ECG monitoring, and its interfaces with an external programming device and an external portable device, which further communicates with the remote service center.

FIG. 1 shows a block diagram of an implantable device 10 for subcutaneous ECG monitoring, and its interfaces with an external programmer 12 and an external portable device 14, which further communicates with the remote service center 16. A similar apparatus, yet with different application for semi-automatic atrial defibrillation, has been described in U.S. Pat. Appl. No. US2007/0265667 filed by the present assignee.

Refer to FIG. 1. The implantable device 10 consists of an electronic circuitry that is hermetically sealed inside a Can, which is made from a biocompatible conductive material such as titanium, a non-conductive header attached to the Can, two or more sensing electrodes 18, with or without leads connected to the header.

The sensing electrodes 18, which are electrically isolated from one another, are mounted over the outer surface of the Can, or outside the header, or at the distal end of the leads (if available). For subcutaneous ECG recording, one or more pairs of sensing electrodes 18 form the sensing vectors and the inter-electrode distance is preferably greater than 3 cm.

The leads are optional for subcutaneous ECG recording. Generally, if the measured subcutaneous ECG amplitude is too small for reliable sensing, despite configuring different sensing vectors and recording at different anatomical locations, then one or more subcutaneous leads (with distal electrodes) could be tunneled under the patient's skin and connected to the header, so that larger subcutaneous ECG amplitude could be measured by increasing inter-electrode distance, e.g., between the lead electrode and the Can or header electrode.

Still refer to FIG. 1. Enclosed inside the hermetically sealed Can, a microprocessor 20 and associated circuitry make up the controller of the implant device 10. The implant device 10 is powered by a battery 22, and maintains an internal clock 24 for timing the operations. The microprocessor 20 communicates with a memory 26 via a bi-directional data bus. The memory 26 typically comprises a ROM or RAM for program storage and a RAM for data storage.

The sensing electrodes 18 are first connected to an electronic interface 28 that preferably includes a feedthrough circuitry for noise reduction, a high voltage protection circuitry, a switch network circuitry for sensing channel selection, and front-end analog filters, as well known in the field.

The configurations of the interface circuitry 28 (e.g., filter settings, sensing channel selection, etc.) can be programmed by the microprocessor 20.

The microprocessor 20 connects to an I/O control unit 30 to manage the input and output of the implant device 10. One input signal is the subcutaneous ECG picked up by the sensing electrodes 18. After pre-processed by the interface circuitry 28, the subcutaneous ECG signal is further processed by the ECG sensing unit 32, which usually consists of amplifiers, analog-to-digital converters, digital filters, etc., as known in the art.

Another input signal is the impedance (Z) signal measured between the sensing electrodes 18 by an impedance measurement unit 34. By injecting a small constant current (e.g., 100 uA, preferably biphasic) between two electrodes 18 while measuring the voltage difference between the same or different pair of electrodes 18, the impedance is calculated as the ratio between the measured voltage difference and the injecting current strength. As known in the art, the impedance signal provides useful information on the integrity of the sensing channel. In addition, the continuously measured impedance signal may be further processed by the microprocessor 20 to extract other physiological status of the patient, such as the respiration rate.

Other types of biological signals measured by specific sensors can also serve as input to the implant device 10. For example, an on-board accelerometer can serve as a motion sensor 36 that provides patient's activity signal to the implant device 10, an on-board (or embedded in the lead) temperature sensor 38 can provide the subcutaneous temperature signal to the implant device 10. Other types of input signals include, but are not limited to, the subcutaneous pressure signal measured by a pressure sensor, the acoustic signal measured by an acoustic sensor, the subcutaneous pH signal measured by a pH sensor, etc.

By running the program stored in the memory 26, the microprocessor 20 also sends instructions to the ECG sensing unit 32, the impedance measurement unit 34, and other input measurement units to control how these signals are acquired (e.g., gain, offset, filter settings, sampling frequency, sampling resolution, etc.).

The acquired biological signals are then stored in the device memory 26 and analyzed by the microprocessor 20 by running programmed algorithms. For example, the microprocessor 20 continuously analyze the acquired subcutaneous ECG signals to detect the peak of QRS complex. Such QRS peak detection can be achieved by many different means. In a preferred embodiment, the QRS peak detection is achieved by using an Auto-Sensing algorithm that automatically adjust the sensing threshold, which is adaptive to the measured peak amplitude of the QRS complex and varies based on a predetermined time dependence. One exemplary Auto-Sensing algorithm has been disclosed in U.S. Pat. No. 5,891,048, assigned to the present assignee.

Accordingly, the implant device 10 measures the intervals between any two adjacent peaks of the detected QRS complexes, and these intervals are termed RR intervals. These measured RR intervals are stored in the device memory 26 according to predefined storage modes. One typical mode is the queue-loop mode, meaning the measured RR intervals are stored in a predefined memory space, and while the allocated memory space is full, the newly measured RR intervals replace the oldest stored RR interval data. Another typical mode is the snapshot mode, meaning the measured RR intervals are stored in a predefined memory space, and while the allocated memory space is full, the newly measured RR intervals are not stored until the microprocessor 20 decides to store another episode of RR intervals. Yet another typical mode is the mixed mode, in which one or more segments of allocated memory space store the RR intervals in queue-loop mode, whereas one or more segments of separately allocated memory space store the RR intervals in snapshot mode.

Similarly, the microprocessor 20 can also continuously analyze the acquired subcutaneous ECG signals to measure other metrics of the QRS complex, such as the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex, and so on. Likewise, the time series of these measured metrics are stored in the device memory 26 for further analysis.

The implant device 10 also includes a radio-frequency (RF) telemetry unit 40. The RF telemetry unit 40 may be of the type well known in the art for conveying various information which it obtains from the implant device 10 to the external programmer 12, or for receiving programming parameters from the external programmer 12 and then conveys to the implant device 10. In one typical embodiment, the external programmer 12 can interrogate the implant device 10 to get the status of the implant device 10 (e.g., battery status, sensing channel impedance, etc.) or the data recorded by the implant device 10 (e.g., peak amplitude of the QRS complexes, statistics of measured RR intervals, etc.). In another typical embodiment, the external programmer 12 can be used to activate or deactivate selected algorithms or update programmable parameters of the implant device 10.

In addition, the external portable device 14 to be described hereinafter, can also communicate bi-directionally with the implant device 10 through the telemetry unit 40. Preferably, the data that may be received from or sent to the external portable device 14 are more limited as compared to the data that may be received from or sent to the external programmer 12.

In a preferred embodiment, the data that are transmitted from the external portable device 14 to the implant device 10 are simple commands, such as trigger a snapshot of the acquired subcutaneous ECG, retrieve most recently diagnostic information from the implanted device 10, etc. These commands set the implant device 10 into one of a number of modalities wherein each modality is determined and controlled by parameters that can only be selected by a physician operating the external programmer 12 using secure password or codes.

The data that are transmitted from the implant device 10 to the external portable device 14 preferably include simple acknowledgment to confirm receiving the commands from the external portable device 14, the signals warning the detection of abnormal conditions, such as detection of atrial fibrillation (AF), detection of high ventricular rate (HVR), detection of low ventricular rate (LVR), detection of abnormal sensing impedance, detection of abnormal temperature, and so on. Other diagnostic information, such as the AF burden, the frequency of ectopic beats, snapshots of RR intervals or subcutaneous ECG, etc., can also be transmitted to the external portable device 14. Preferably, a physician operating the external programmer 12 using secure password or codes controls the enable or disable condition as well as the amount of data that can be transmitted from the implant device 10 to the external portable device 14.

Still refer to FIG. 1. The external portable device 14 has a power source 42, such as a lithium battery, which provides power to the electrical components of the device 14. The battery 42 is chargeable by connecting to an external charger 44. The external portable device 14 also maintains an internal clock 46 for timing its operations. The overall functioning of the external portable device 14 is controlled by its microprocessor 48, which reads and performs instructions stored in its associated memory 50. The instructions stored in memory 50 preferably include instructions defining a communication protocol compatible with the implant device 10, and instructions defining a communication protocol compatible with the remote service center 16.

The microprocessor 48 of the external portal device 14 communicates with an I/O control unit 52 to read from the keypad 54 (or press switches) the patient input commands. In an exemplary embodiment, one subset of the input commands is designed to configure the external portable device 14, for example, to turn on or off certain outputs 56 as described hereinafter, or select specific communication protocols. Another subset of the input commands is designed to establish communication between the external portable device 14 and the remote service center 16 through remote communication unit 58. For example, patient's input 54 can command the external portable device 14 to transmit diagnostic information (retrieved from the implant device 10) to the remote service center 16, and wait to receive acknowledgement. The third subset of the commands is designed to establish communication between the external portable device 14 and the implant device 10 through implant communication unit 60. For example, patient's input 54 can command the external portable device 14 to transmit corresponding signals to the implant device 10 to trigger recording a snapshot of the subcutaneous ECG, to retrieve diagnostic information from the implanted device 10, etc. The implant communication unit 60 also receives the acknowledgement and related diagnostic information sent from the implant device 10, and conveys these data to the microprocessor 48 for storage in the memory 50.

According to one exemplary embodiment of the present invention, upon receiving a predefined warning signal from the implant device 10 (e.g., detection of AF, detection of HVR, detection of LVR, detection of abnormal sensing impedance, detection of abnormal temperature, etc.), the microprocessor 48 of the external portable device 14 communicates with the I/O control unit 52 to generate output 56 that is perceptible by the patient. Such output 56 can be in the form of visible message, such as the light-up or blinking of a light emitting diode (LED) or the text message displayed in a liquid crystal display (LCD), or in the form of audible message such as beep, ringing tone, or pre-recorded voice messages played by a speaker, or in the form of discernible vibration by a vibrator. According to the patient's preference, one or multiple types of warning message can be respectively turned on or off. For example, the visible warning message can be turned on while the audible warning message can be turned off during the night if the patient chooses not to be disturbed during sleep even if the implant device 10 detects AF. Besides generating warning messages, some diagnostic information that is received from the implant device 10 and stored in memory 50 (e.g., the heart rate) can also be provided to the patient in the form of visual or audible messages.

The external portable device 14, via its remote communication unit 58, can further communicate with the remote service center 16. Such long-range communication apparatus can be in the form of a mobile radio network, or a fixed-line telecommunication network, or the internet, as well known in the art. Examples of such long-range communication apparatus have been taught in U.S. Pat. No. 6,470,215, U.S. Pat.

No. 6,574,509, U.S. Pat. No. 6,622,043, all are assigned to the assignee of the present invention and incorporated herein by reference.

In one typical embodiment, the external portable device 14 transmits the implant device status information (e.g., battery status, sensing impedance, etc.) as well as relevant diagnostic information (e.g., AF burden, Ectopic Beat frequency, etc.) to the remote service center 16 according to a predefined transmission frequency and schedule (e.g., every midnight, etc.). Yet in another typical embodiment, the external portable device 14 communicates with the remote service center 16 in a trigger mode, for example, upon receiving a warning signal from the implant device 10, or upon the patient trigger. In such cases, the external portable device 14 transmits critical diagnostic information stored in memory 50 (e.g., AF burden, mean heart rate, the subcutaneous ECG snapshot, etc.) to the remote service center 16.

The remote service center 16 receives the information via compatible communication protocols, then sends acknowledgement back to the external portable device 14, which may generate visible or audible output 56 indicating receipt of the acknowledgement. The data received by the remote service center 16 is stored in central database, and is promptly presented to the patient's physician or responsible expert through proper means, such as fax or email as known in the art. By reviewing the received diagnostic information, the physician can evaluate the patient's condition and provide expert advice to the patient who wishes to contact the physician in response to the warning signals generated by the external portable device 14.

The method to detect abnormal cardiac intervals using morphological operators is disclosed hereinafter.

According to a preferred embodiment of this invention, the implant device 10 continuously senses the subcutaneous ECG signals, detects the peak of QRS complex, and measures the RR intervals. The device 10 also maintains a first-in-first-out (FIFO) running buffer that stores the measured RR intervals of the most recent L cardiac cycles, where L is a predefined parameter that can be programmed through the external programming device.

According to another embodiment of this invention, the device 10 continuously senses the subcutaneous ECG signals, detects the peak of QRS complex, and derives one or more metrics from the QRS complex. These metrics include but are not limited to, the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex, and so on. Similarly, the device 10 maintains a FIFO running buffer that stores the derived metrics of the most recent L cardiac cycles, where L is a predefined parameter that can be programmed through the external programming device.

Also according to this invention, morphological operators are implemented, either in embedded software or in hardware platform of the device 10. As described in details later, these morphological operators are applied to the measured RR intervals, to remove the abnormal RR intervals to get the trend of RR intervals, and detect the abnormal RR intervals, including but are not limited to Ectopic Beats, episode of NSVT, sudden RR pauses, etc.

According to this invention, the device 10 calculates and maintains a plural of statistics based on the detected abnormal RR intervals, including but are not limited to, the Ectopic Beat counter, the Ectopic Beat frequency, etc. In addition, the filtered RR intervals (without abnormal RR intervals) are used to calculate the conventional HRV parameters, such as the SDANN, pNN50, as well known in the art. The baseline heart rate, circadian variation of the heart rate, and the heart rate trend are also measured based on the filtered RR intervals (i.e., free of abnormal RR intervals). Furthermore, the HRT after Ectopic Beat can also be calculated and logged by the device 10.

Now the concept of morphological operators is described. There are two basic morphological operators: erosion and dilation. These basic operators are usually applied in sequence that yields two derived morphological operations: opening and closing.

Denote $F=[f_0, f_1, \ldots, f_{N-1}]$ the discrete input signal, and denote $K=[k_0, k_1, \ldots, k_{M-1}]$ a predefined discrete kernel function, also called structure element (SE), where N and M are two integers that N>M.

The erosion of the signal F by the structure element K, denoted $F \ominus K$, is defined as:

$$F \ominus K(i) = \min_{j=0,\ldots,M-1} f_{i+j} - k_j \quad \text{for } i = 0, 1, \ldots, N-M$$

The erosion is a shrinking operation in that values of $F \ominus K$ are always less than those of F if all elements of the SE are greater than zero. FIG. 2A shows the circuit block diagram of implementing the erosion operator. The input signal passes through a cascade of delay units 100, 100' and 100". The structuring elements 102, 102' and 102" and 102''' are subtracted from the input samples with corresponding delay taps 104, 104', 104" and 104'''. For each snapshot of the input signal with segment length M, one output sample is generated, by finding the minimum 106 of the subtracted values. Note that compared to the input signal, the erosion output is delayed by M−1 taps. Also note that if SE is an all zero vector, than the subtraction operation is not needed.

The dilation of the signal F by the structure element K, denoted $F \oplus K$, is defined as:

$$F \oplus K(i) = \max_{j=i-M+1,\ldots,i} f_j + k_{i-j} \quad \text{for } i = M-1, M, \ldots, N-1$$

The dilation is an expansion operation in that values of $F \oplus K$ are always larger than those of F if all elements of the SE are greater than zero. FIG. 2B shows the circuit block diagram of implementing the dilation operator. The input signal passes through a cascade of delay units 150, 150' and 150". The structuring elements 152, 152' and 152" and 152''' are reversed and then added to the input samples with corresponding delay taps 154, 154', 154" and 154'''. For each snapshot of the input signal with segment length M, one output sample is generated, by finding the maximum 156 of the added values. Note that compared to the input signal, the dilation output has no time delay. Also note that if SE is an all zero vector, than the addition operation is not needed.

As illustrated in FIG. 3A, opening of a data sequence by a SE is defined as erosion 202 followed by a dilation 204. The opening of a data sequence can be interpreted as sliding the SE along the data sequence from beneath and the result is the highest points reached by any part of the SE. As further illustrated in FIG. 3B, closing of a data sequence by a SE is defined as dilation 204' followed by an erosion 202'. The closing of a data sequence can be interpreted as sliding a 'flipped-over' version of the SE along the data sequence from above and the result is the lowest points reached by any part of the SE.

Figure 4B:
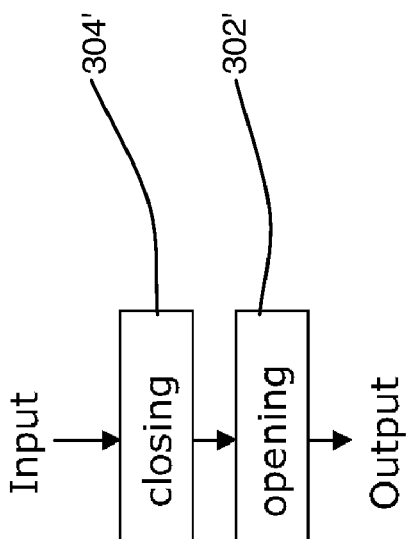
FIG. 4B shows the block diagram of another impulse filter consisting of a closing operation followed by an opening operation.
Figure 4C:
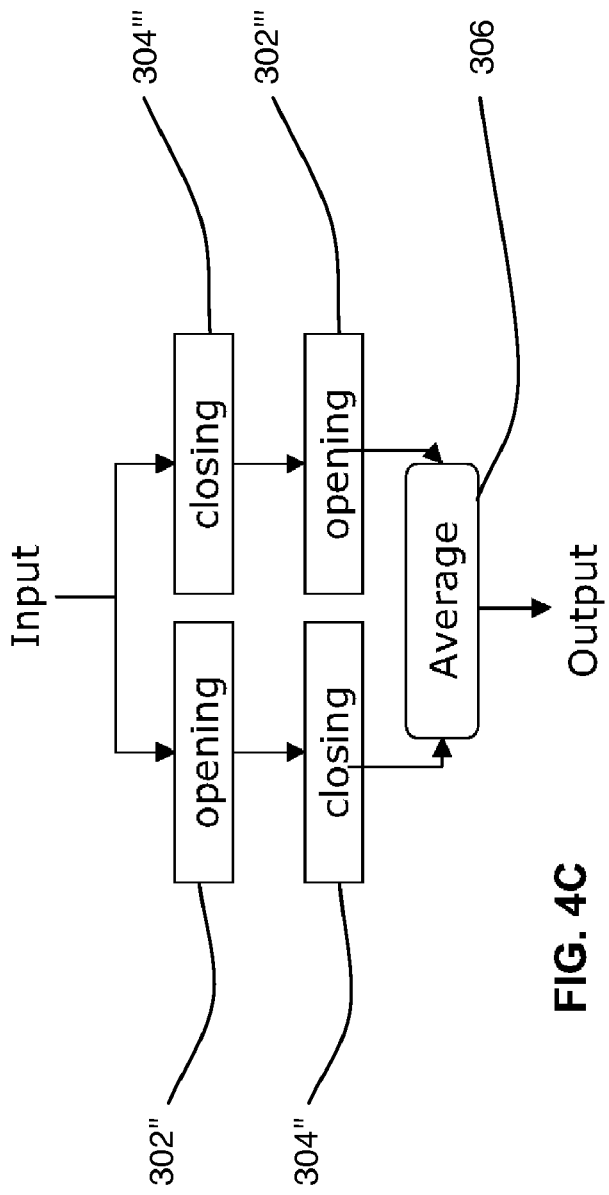
FIG. 4C shows yet another block diagram of an impulse filter in which the opening-closing pair and the closing-opening pair operate in parallel.
Figure 4A:
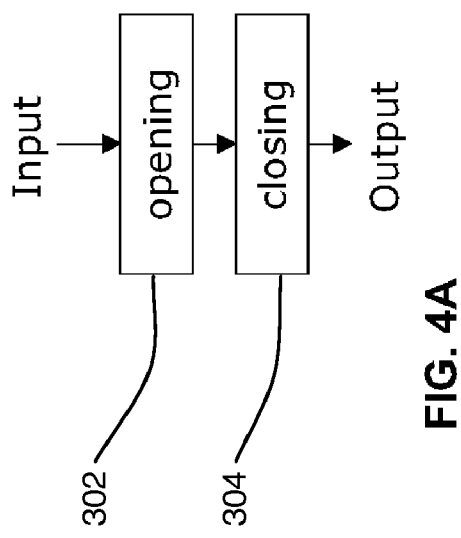
FIG. 4A shows the block diagram of an impulse filter consisting of an opening operation followed by a closing operation.

In typical applications, opening is used to suppress peaks while closing is used to suppress pits. Therefore, in order to suppress both peaks and pits, opening and closing are usually used in pairs. For example, FIG. 4A shows the block diagram of an impulse filter that removes both peaks and pits by applying an opening operation 302 followed by a closing operation 304. Similarly, FIG. 4B shows the block diagram of another impulse filter by applying a closing operation 304' followed by an opening operation 302'. FIG. 4C shows yet another block diagram of an impulse filter that combines the previous two filters. In this case, the opening-closing pair (302" and 304") and the closing-opening pair (304''' and 302''') operate in parallel, and their outputs are averaged (306) to generate the filtered output.

The design of the SE depends on the shape of the signal that is to be preserved. Since the opening and closing operations are intended to remove impulses, the SE must be designed so that the trend of the RR intervals is preserved. A SE is characterized by its shape, width, and height. It has been demonstrated that the width of the SE plays a more important role, compared to either the height or the shape, in determining the impulse suppression performance. In the following description of the embodiments of the present invention, the SE is considered as an all zero vector with predefined width, although it is obvious that other types of SE can be defined.

Now the method to detect abnormal cardiac intervals based on device stored RR intervals is disclosed. Because the abrupt increase or decrease of the abnormal cardiac intervals are usually characterized by positive or negative impulses in the tachogram (termed as impulse RR intervals in the following description), the morphological operators are particularly suitable for detecting these RR interval spikes.

Figure 5:
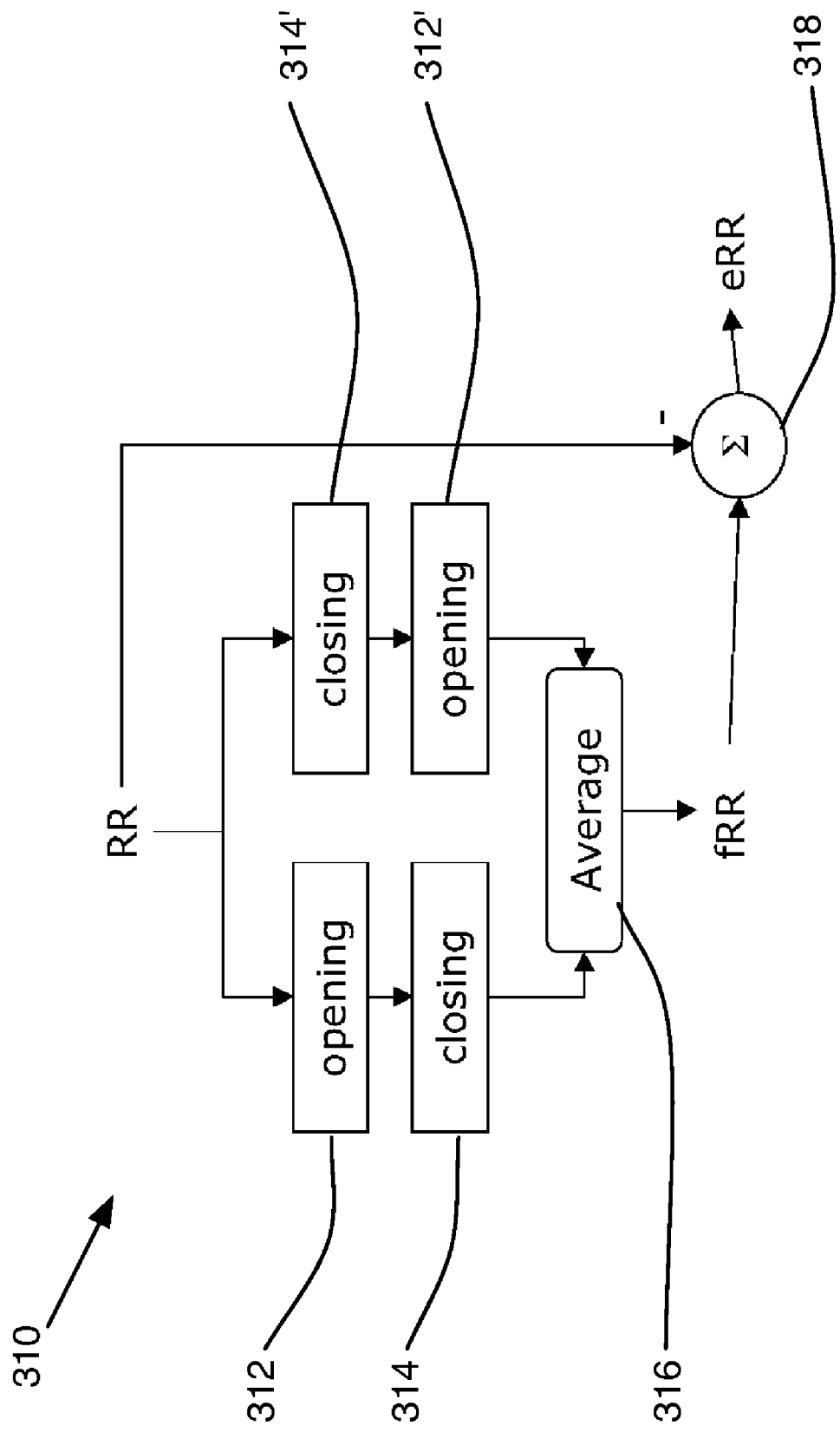
FIG. 5 shows the block diagram of applying a morphological impulse filter to the input RR intervals to obtain the filtered fRR intervals and the difference eRR intervals.

Now refer to FIG. 5. According to this invention, the time series of RR intervals provide input to an impulse filter 310 that forms a second signal analyzer comprising two branches in parallel, opening-closing (312 and 314) and closing-opening (314' and 312'), and their results are averaged (316) to get filtered RR intervals fRR. As indicated in FIG. 4, either branch of the impulse filter can be used alone to obtain fRR. The RR is subtracted from fRR (318) to get their difference intervals eRR.

In a typical embodiment, the structure elements used in all opening and closing operations of the impulse filter 310 shown FIG. 5 are identical. For removal of isolated RR spikes (e.g., ectopic beats, post-Ectopic Beat pauses, etc.), the SE width is preferably short. For example, the SE for the RR impulse filter is preferably defined as a three-zero vector [0, 0, 0]. Also according to the present invention, the SE width for the RR impulse filter is user-programmable or selectable from a predetermined range, e.g., from 3 to 5.

By applying the morphological impulse filter to the RR intervals, the abrupt lengthening and abrupt shortening of the RR intervals (or impulse RR intervals) are removed. Thus the output fRR intervals preserve the trend of the RR intervals without any impulse RR intervals. On the other hand, the eRR intervals quantify the deviation of each RR interval from the corresponding trend interval (fRR). Thus for normal cardiac cycles, eRR intervals are close to zero, whereas for impulse RR intervals, eRR intervals have large (positive or negative) values.

Figure 6:
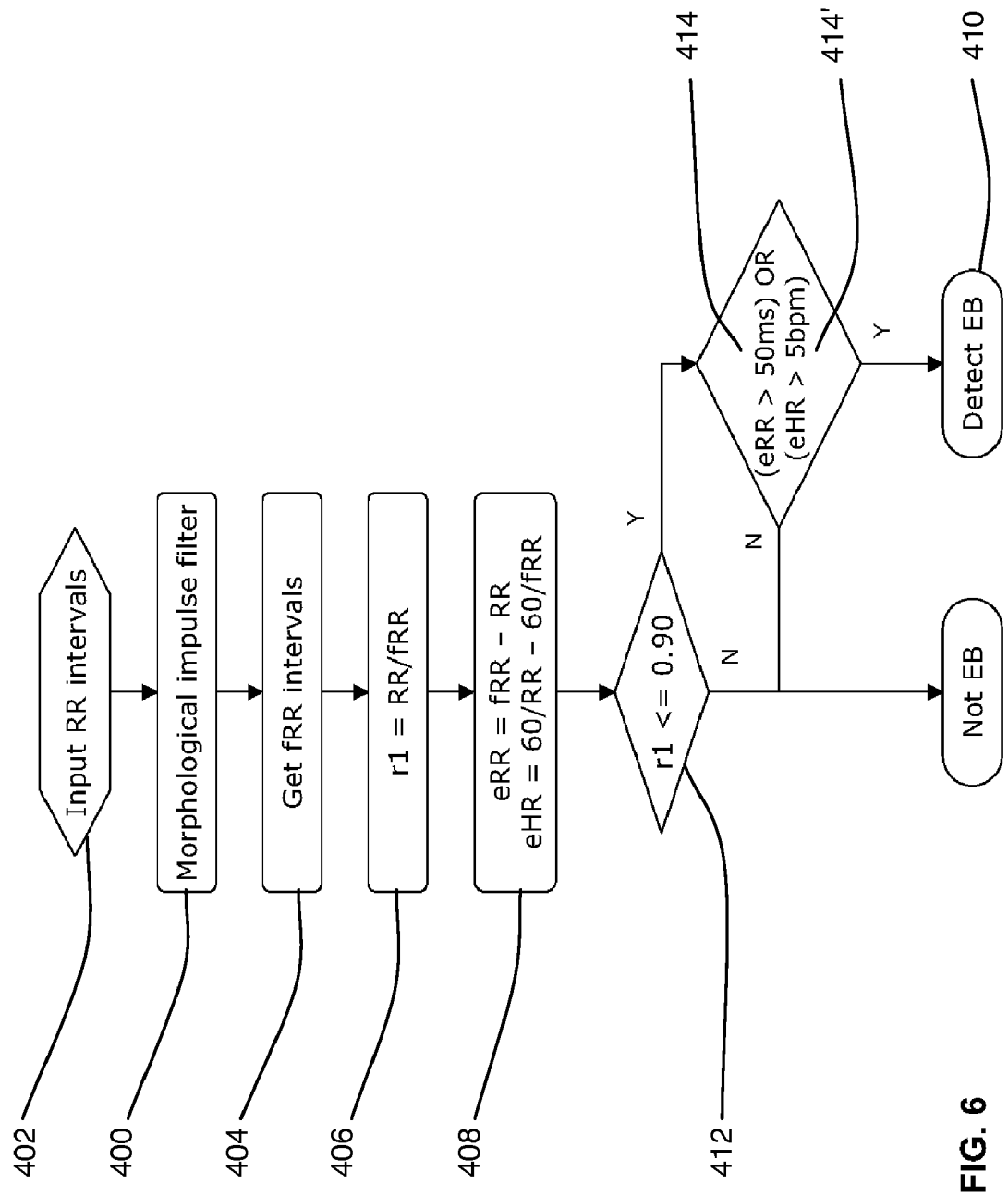
FIG. 6 illustrates an exemplary flowchart for Ectopic Beat detection based on morphological impulse filtering of the RR intervals.

Now refer to FIG. 6, which illustrates an exemplary flowchart for Ectopic Beat detection. Using the morphological impulse filter 400 that is described in FIG. 5, the input RR intervals 402 are continuously processed to generate the corresponding filtered fRR intervals 404. For each input RR interval 402 and the corresponding filtered output fRR interval 404, their ratio r1=RR/fRR (406) is calculated. In addition, the deviation between input RR interval 402 and the corresponding filtered output fRR interval 404 is calculated as eRR=fRR−RR (408). The corresponding heart rate difference is also calculated as eHR=60/RR−60/fRR (408) (assuming eHR unit is bpm, and RR and fRR units are seconds). In one typical embodiment, an Ectopic Beat is detected (410) if two conditions are met: (1) r1 is below a first predefined threshold that is less than 1.0 (412) (e.g., 0.90), and (2) eRR is greater than a second predefined threshold (414) (e.g., 50 ms). In another embodiment, the second condition is replaced by requiring eHR is greater than a third predefined threshold (414') (e.g., 5 bpm). Yet in another embodiment, the second condition is changed to requiring either eRR is greater than a second predefined threshold (414) (e.g., 50 ms), or eHR is greater than a third predefined threshold (414') (e.g., 5 bpm), as shown in the figure. Alternatively, the second condition may be changed to requiring both eRR is greater than a second predefined threshold (414) (e.g., 50 ms), and eHR is greater than a third predefined threshold (414') (e.g., 5 bpm).

Figure 7:
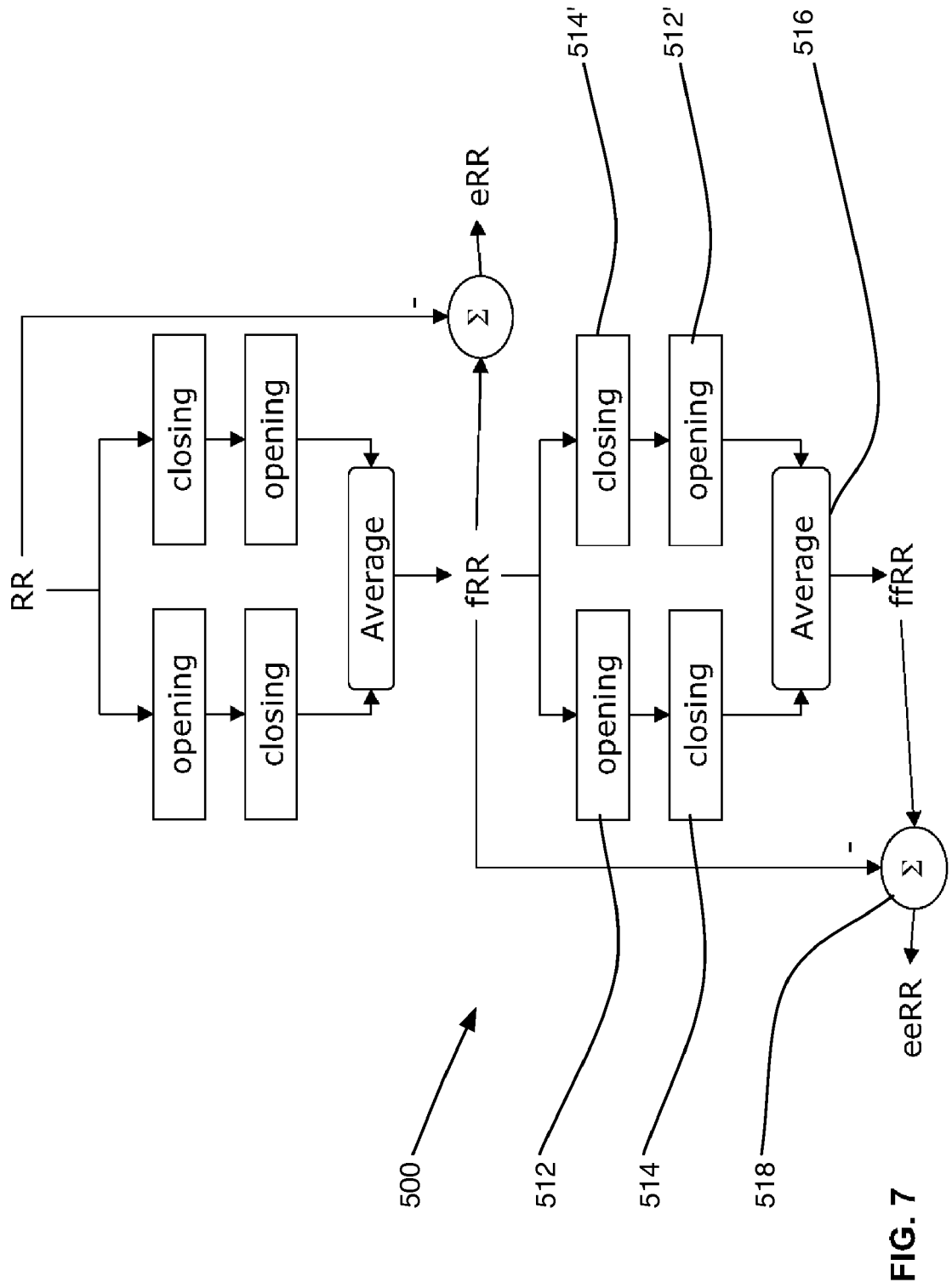
FIG. 7 shows the block diagram of applying a first morphological impulse filter to the input RR intervals to obtain the first filtered fRR intervals and the first difference eRR intervals, and then applying a second morphological filter to the first fRR intervals to obtain the second filtered ffRR intervals and the second difference eeRR intervals.

Now refer to FIG. 7. According to this invention, the initially filtered fRR intervals (free of impulse RR intervals) are further processed by a second morphological impulse filter 500 to detect multiple consecutive abnormal RR intervals. Similarly, this second morphological filter consists of two branches in parallel, opening-closing (512 and 514) and closing-opening (514' and 512'), and their results are averaged (516) to get further filtered intervals termed ffRR. As indicated in FIG. 4, either branch of the impulse filter can be used alone to obtain ffRR. The fRR is subtracted from ffRR (518) to get their difference intervals eeRR.

In a typical embodiment, the structure elements used in all opening and closing operations of the second impulse filter 500 shown FIG. 7 are identical. For removal of multiple consecutive abnormal cardiac intervals (e.g., NSVT episode, or a short run of ventricular pauses), the SE width is preferably longer than the maximum count of consecutive abnormal cardiac cycles. For example, the SE for the RR impulse filter is preferably defined as an 11-zero vector [0, 0, 0, 0, 0, 0, 0, 0, 0, 0, 0]. Also according to the present invention, the SE width for the RR impulse filter is user-programmable or selectable from a predetermined range, e.g., from 7 to 15.

By applying the second morphological filter to the fRR intervals, the multiple consecutive abnormal RR intervals are removed. Thus the output ffRR intervals preserve the trend of the RR intervals without any impulse RR intervals, or any short runs of brady/tachy RR intervals. On the other hand, the eeRR intervals quantify the deviation of each fRR interval from the corresponding trend interval (ffRR). Thus for normal cardiac cycles or impulse RR intervals, eeRR intervals are close to zero, whereas for multiple consecutive abnormal cardiac intervals, eeRR intervals have large (positive or negative) values.

Figure 8:
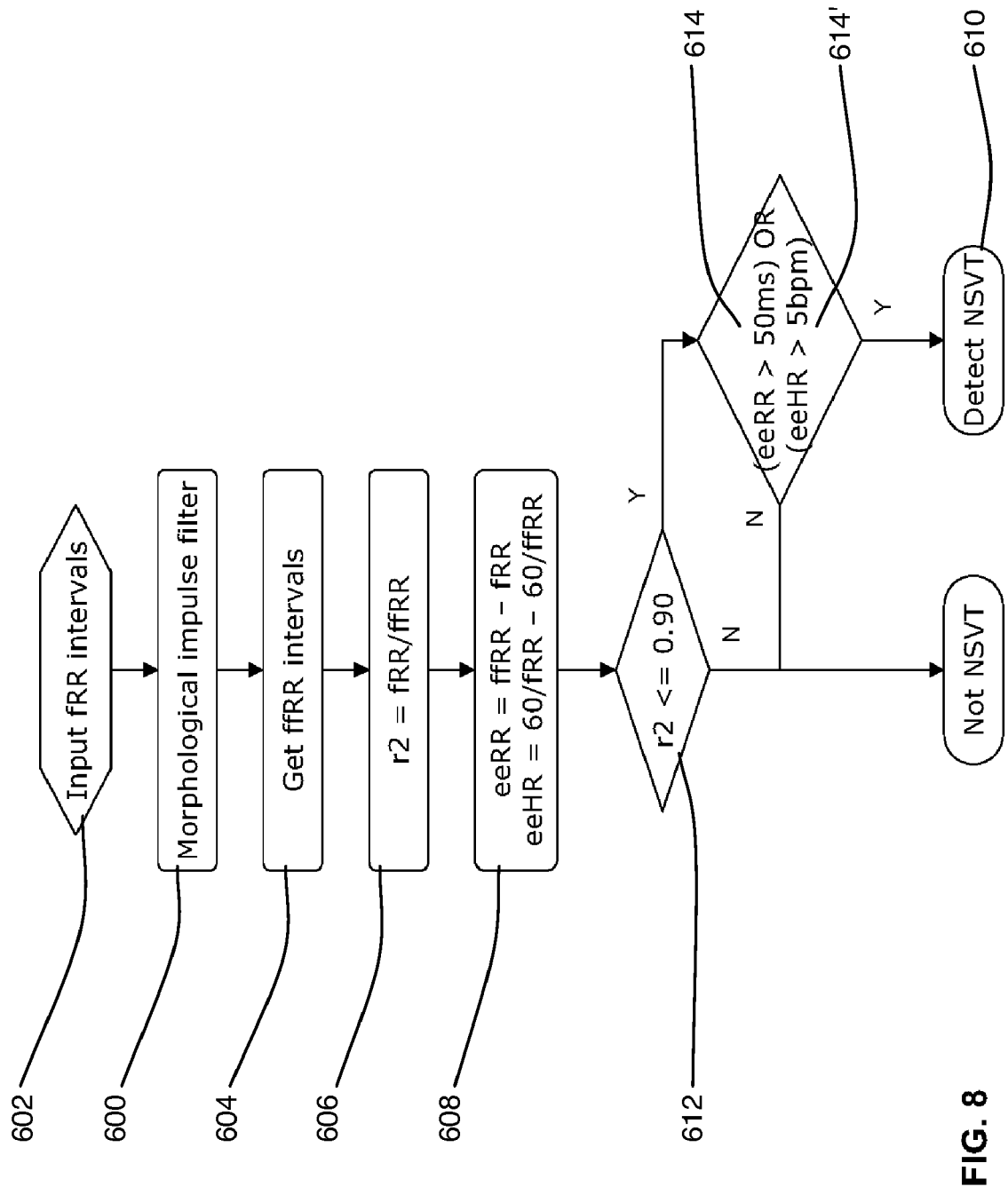
FIG. 8 illustrates an exemplary flowchart for NSVT detection based on morphological impulse filtering of the RR intervals.

Now refer to FIG. 8, which illustrates an exemplary flowchart for NSVT detection. Using the morphological filters 600 that are described in FIG. 7, the input RR intervals 602 are continuously processed to generate the first filtered output fRR intervals and the second filtered output ffRR intervals 604. For each fRR interval and the corresponding ffRR interval, their ratio r2=fRR/ffRR is calculated (606). In addition, the deviation between fRR interval and the corresponding ffRR interval is calculated as eeRR=ffRR−fRR (608). The corresponding heart rate difference is also calculated as eeHR=60/fRR−60/ffRR (608) (assuming eeHR unit is bpm, and fRR and ffRR units are seconds). In one typical embodiment, an episode of NSVT is detected (610) if two conditions are met: (1) r2 is below a first predefined threshold that is less than 1.0 (612) (e.g., 0.90), and (2) eeRR is greater than a second predefined threshold (614) (e.g., 50 ms). In another embodiment, the second condition is replaced by requiring eeHR is greater than a third predefined threshold (614') (e.g., 5 bpm). Yet in another embodiment, the second condition is changed to requiring either eeRR is greater than a second predefined threshold (614) (e.g., 50 ms), or eeHR is greater than a third predefined threshold (614') (e.g., 5 bpm), as shown in the figure. Alternatively, the second condition may be changed to requiring both eeRR is greater than a second predefined threshold (614) (e.g., 50 ms), and eeHR is greater than a third predefined threshold (614') (e.g., 5 bpm).

FIGS. 9-22 show some examples of applying morphological filters to RR intervals.

Figure 9:
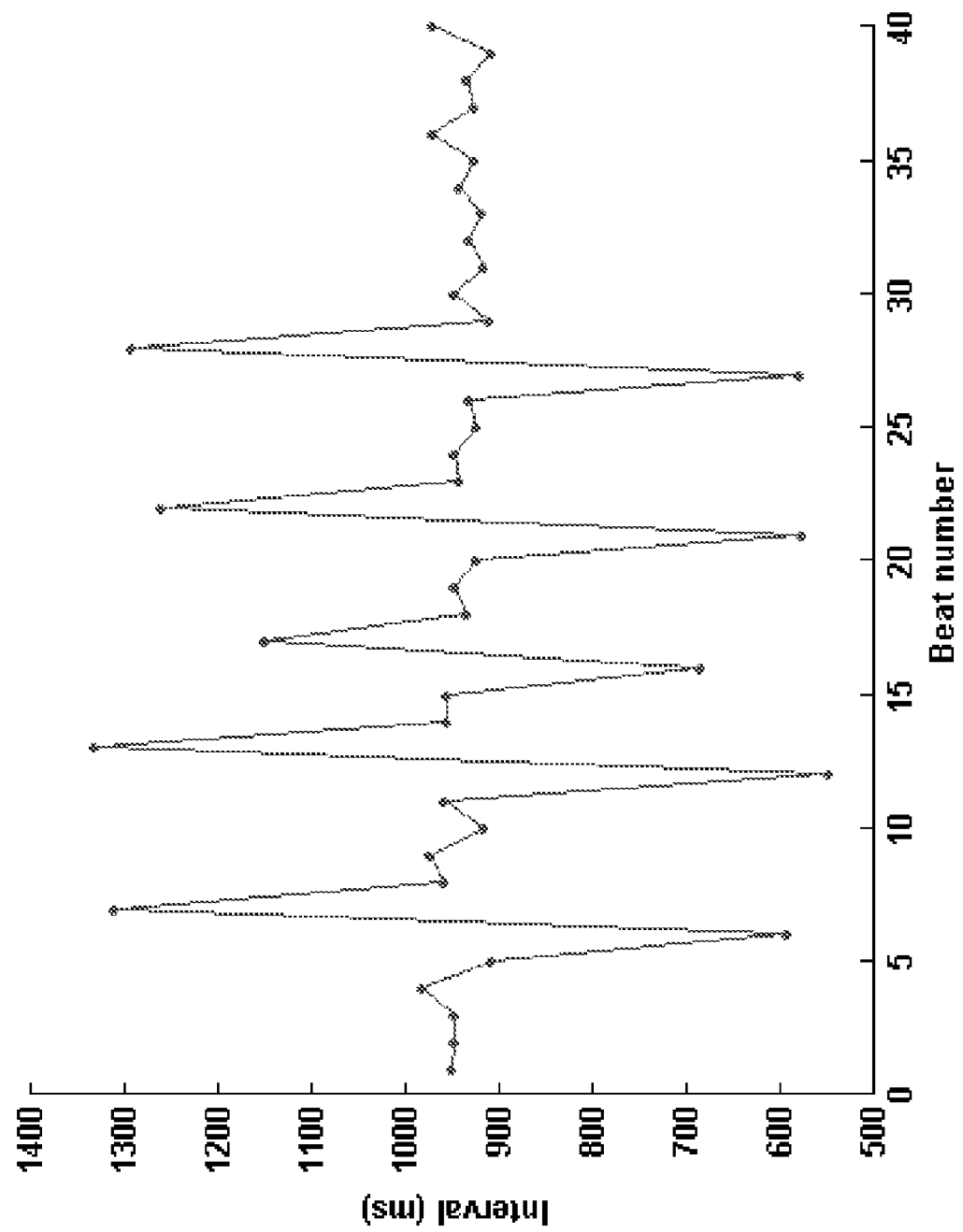
FIG. 9 shows an exemplary segment of RR intervals that include ventricular Ectopic Beats and corresponding post-Ectopic Beat pauses.

FIG. 9 shows an exemplary tachogram of 40 RR intervals that include 5 ventricular Ectopic Beats and 5 corresponding post-Ectopic Beat pauses.

Figure 10:
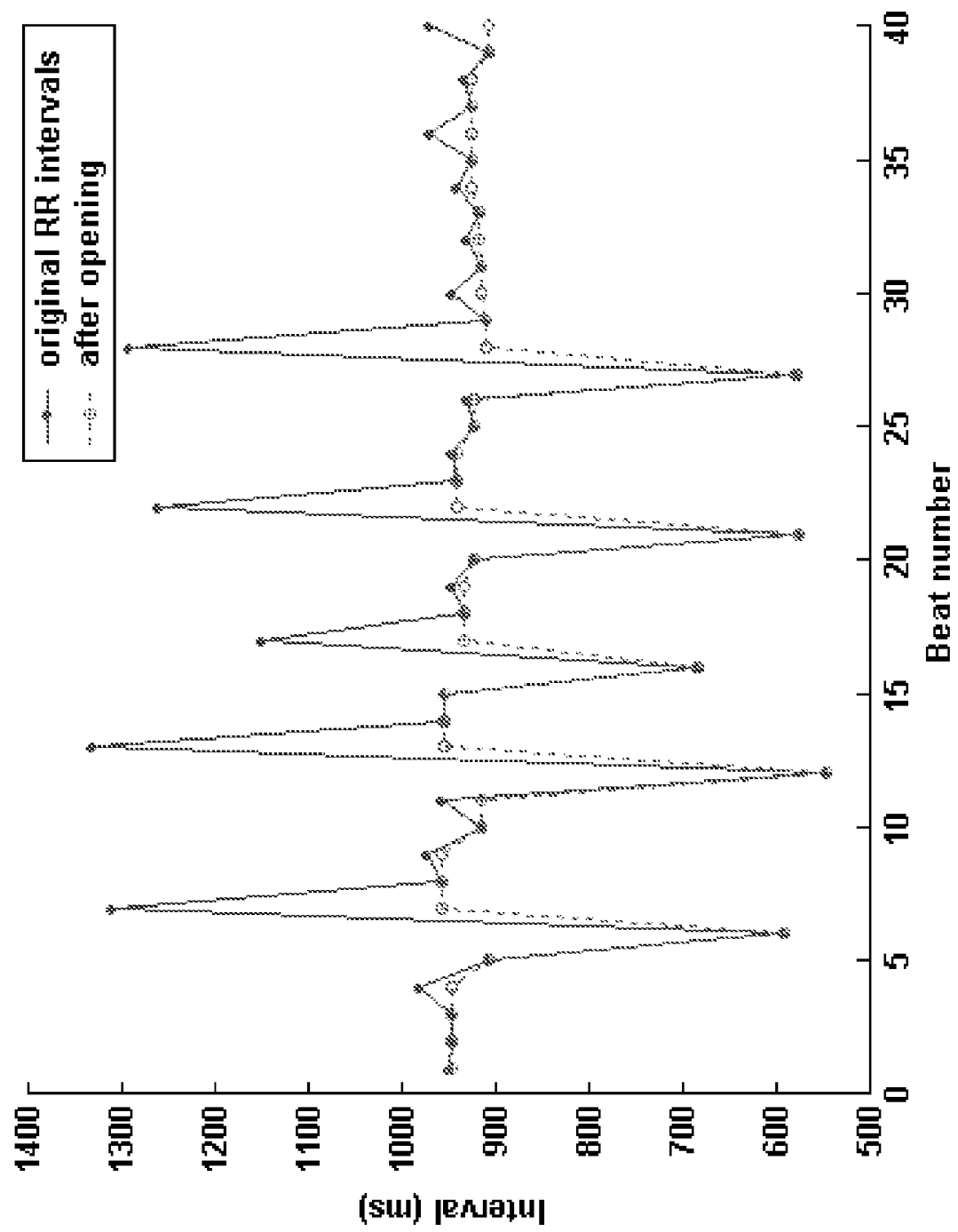
FIG. 10 shows the original RR intervals, together with the filtered RR intervals after applying the opening operator.
Figure 11:
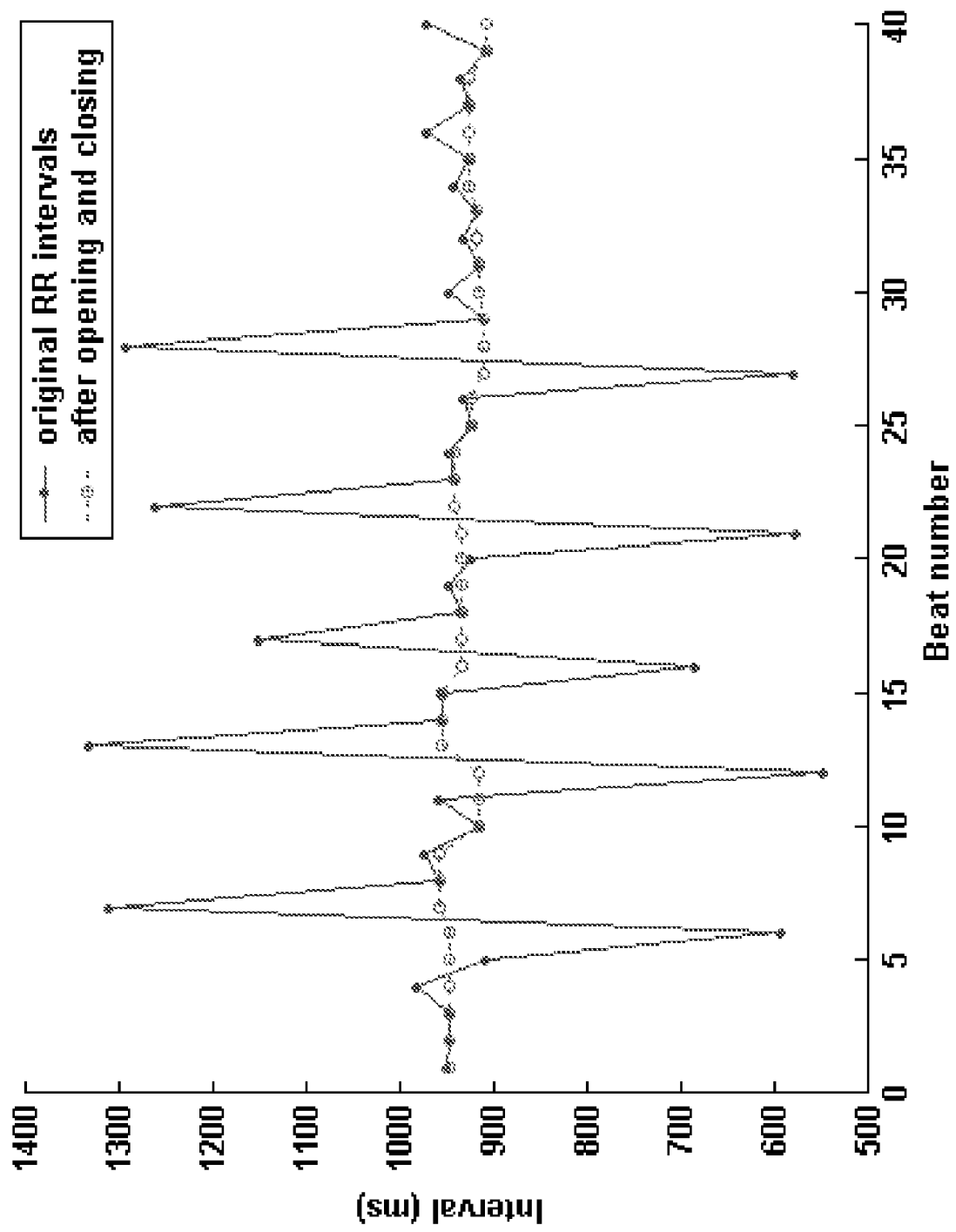
FIG. 11 shows the original RR intervals, together with filtered RR intervals after applying the opening operator followed by the closing operator.

FIG. 10 shows the original 40 RR intervals, together with the filtered RR intervals after applying the opening operator (with a three-zero SE in this example). Clearly, the positive RR peaks are removed after the opening operation. FIG. 11 shows the original 40 RR intervals, together with filtered RR intervals after applying first the opening operator (with a three-zero SE in this example) then by the second closing operator (with a three-zero SE in this example). Clearly, both positive RR peaks and negative RR pits are removed after the opening-closing operations.

Figure 12:
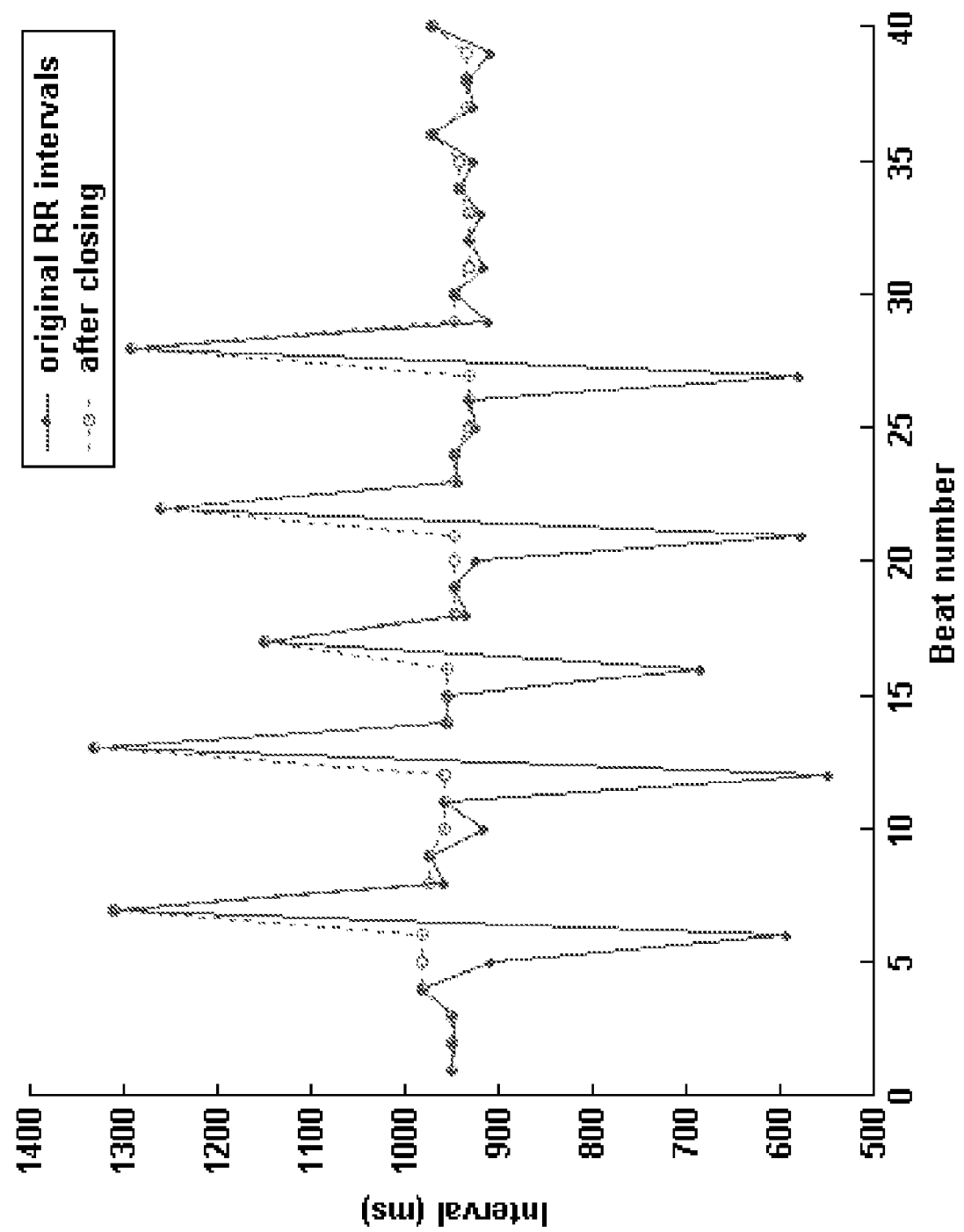
FIG. 12 shows the original RR intervals, together with the filtered RR intervals after applying the closing operator.
Figure 13:
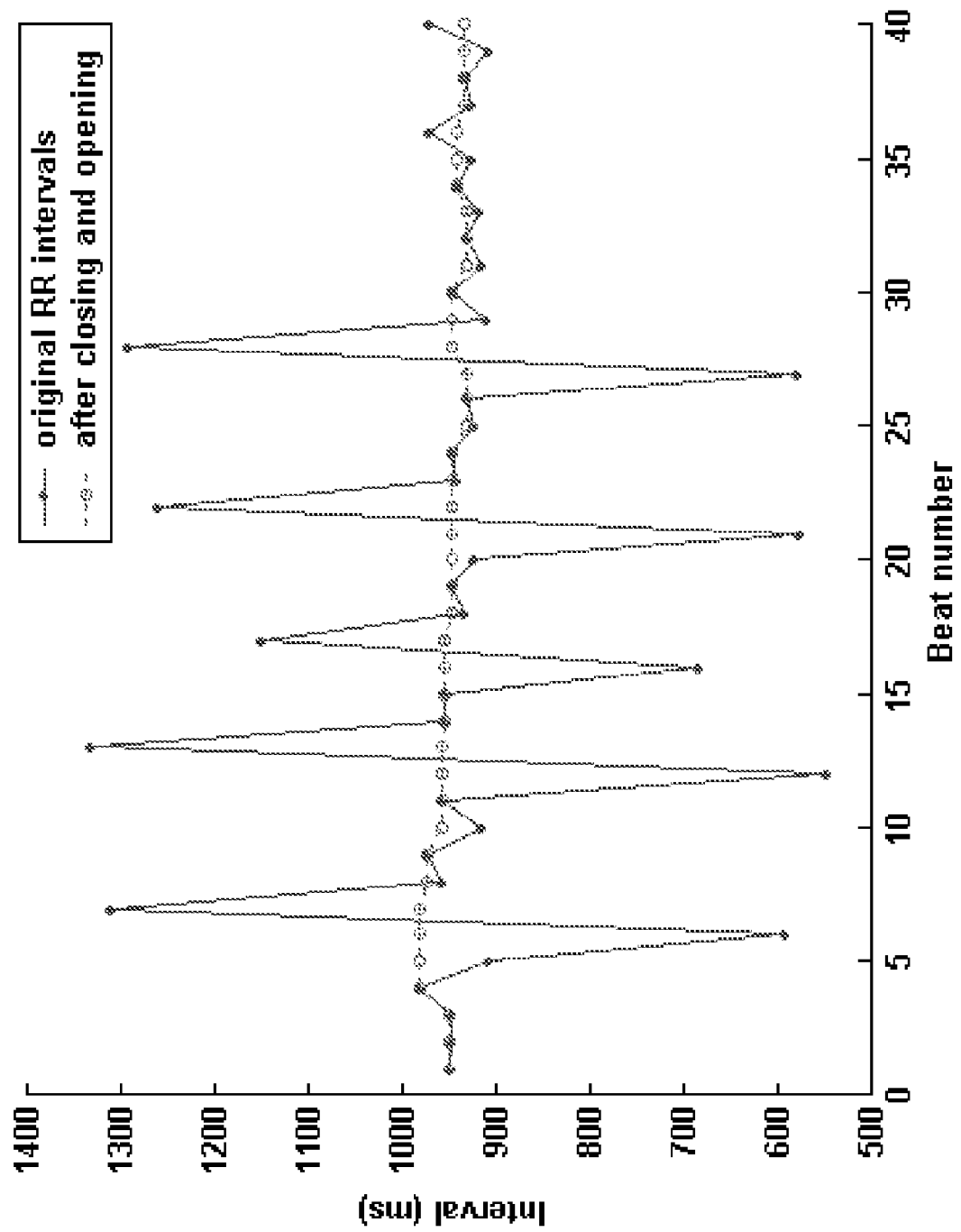
FIG. 13 shows the original RR intervals, together with filtered RR intervals after applying the closing operator followed by the opening operator.

FIG. 12 shows the original 40 RR intervals, together with the filtered RR intervals after applying the closing operator (with a three-zero SE in this example). Clearly, the negative RR pits are removed after the closing operation. FIG. 13 shows the original 40 RR intervals, together with filtered RR intervals after applying first the closing operator (with a three-zero SE in this example) then by the second opening operator (with a three-zero SE in this example). Clearly, both positive RR peaks and negative RR pits are removed after the opening-closing operations.

Figure 14:
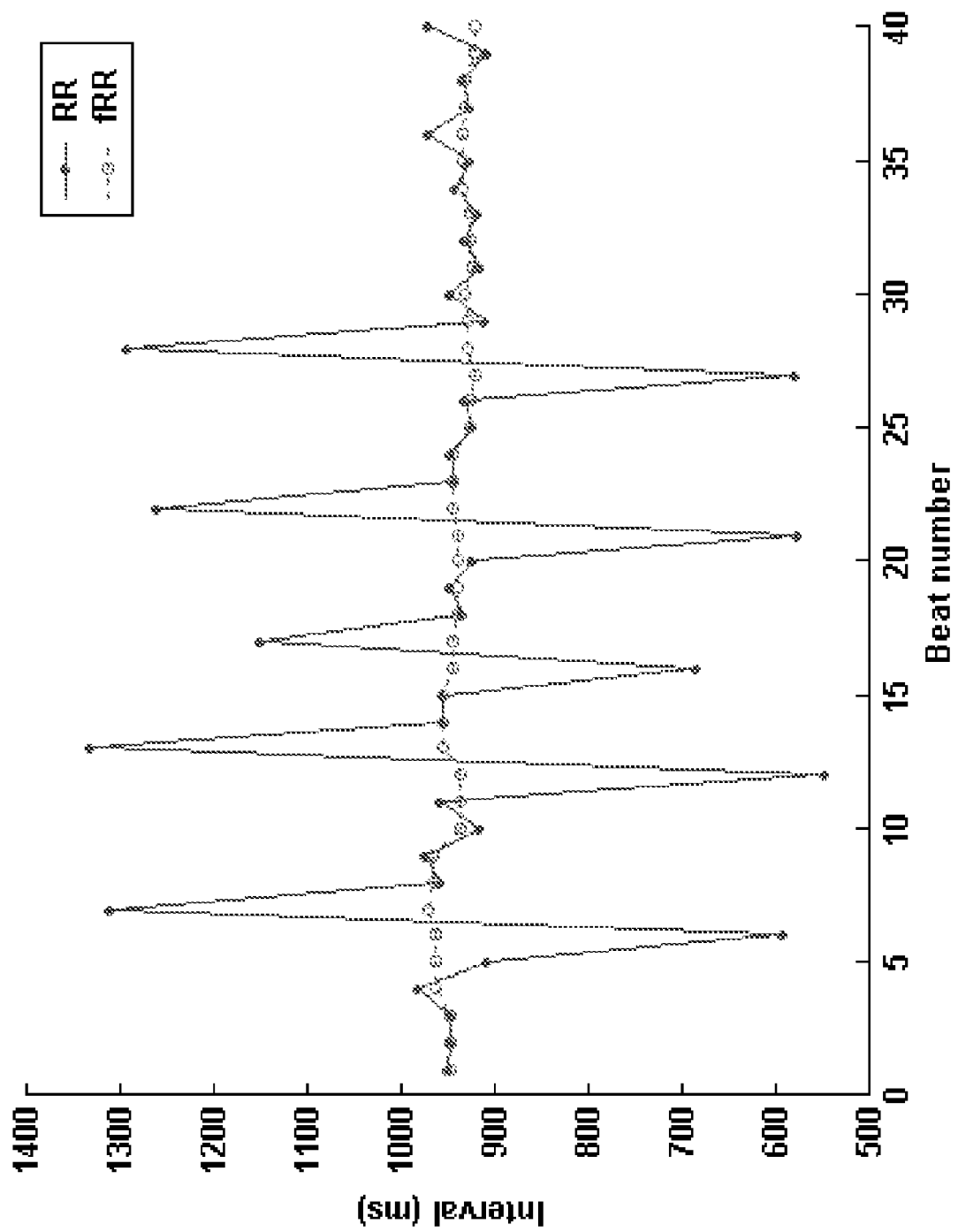
FIG. 14 shows the original RR intervals, together with the filtered intervals fRR after applying the impulse filter illustrated in FIG. 5.

FIG. 14 shows the original 40 RR intervals, together with the filtered intervals fRR after applying the impulse filter illustrated in FIG. 5, where the impulse filter consists of two branches in parallel, opening-closing and closing-opening, and their results are averaged to get the filtered intervals fRR. Clearly, both positive RR peaks and negative RR pits are filtered out in fRR intervals. Compared to FIG. 11 and FIG. 13, the filtered output fRR (averaged results from two parallel branches) is less biased and better preserves the RR trend information.

Figure 15:
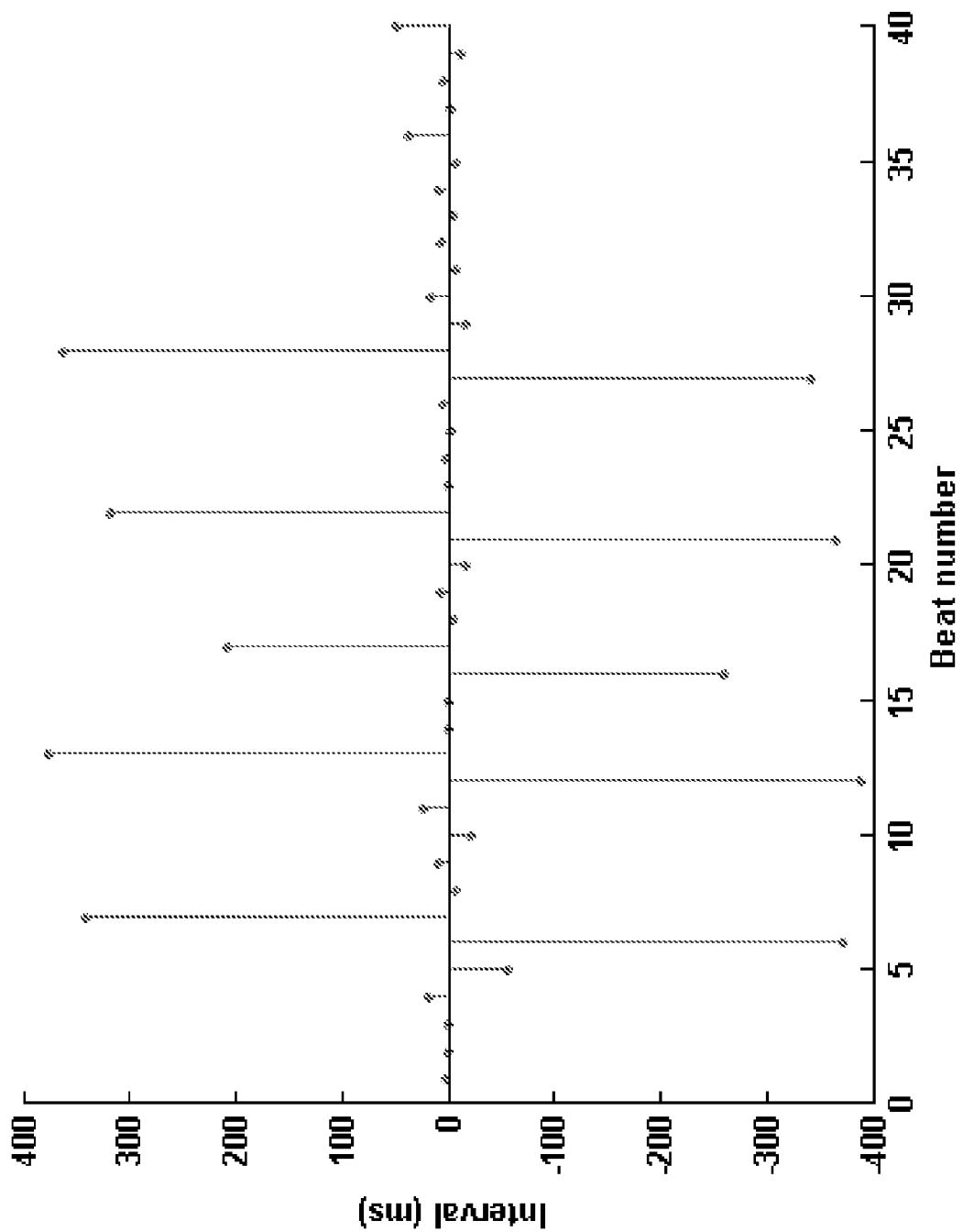
FIG. 15 shows the difference intervals between the original RR intervals and their corresponding filtered fRR intervals.

FIG. 15 shows the difference intervals RR-FRR, that is, the difference between the original 40 RR intervals and their corresponding filtered intervals fRR (note the difference intervals plotted in this figure is the negative of eRR=fRR−RR). The ventricular Ectopic Beats are clearly identified by the 5 negative spikes of the difference intervals, whereas the post-Ectopic Beat pauses are clearly identified by the 5 positive spikes of the difference intervals.

Figure 16:
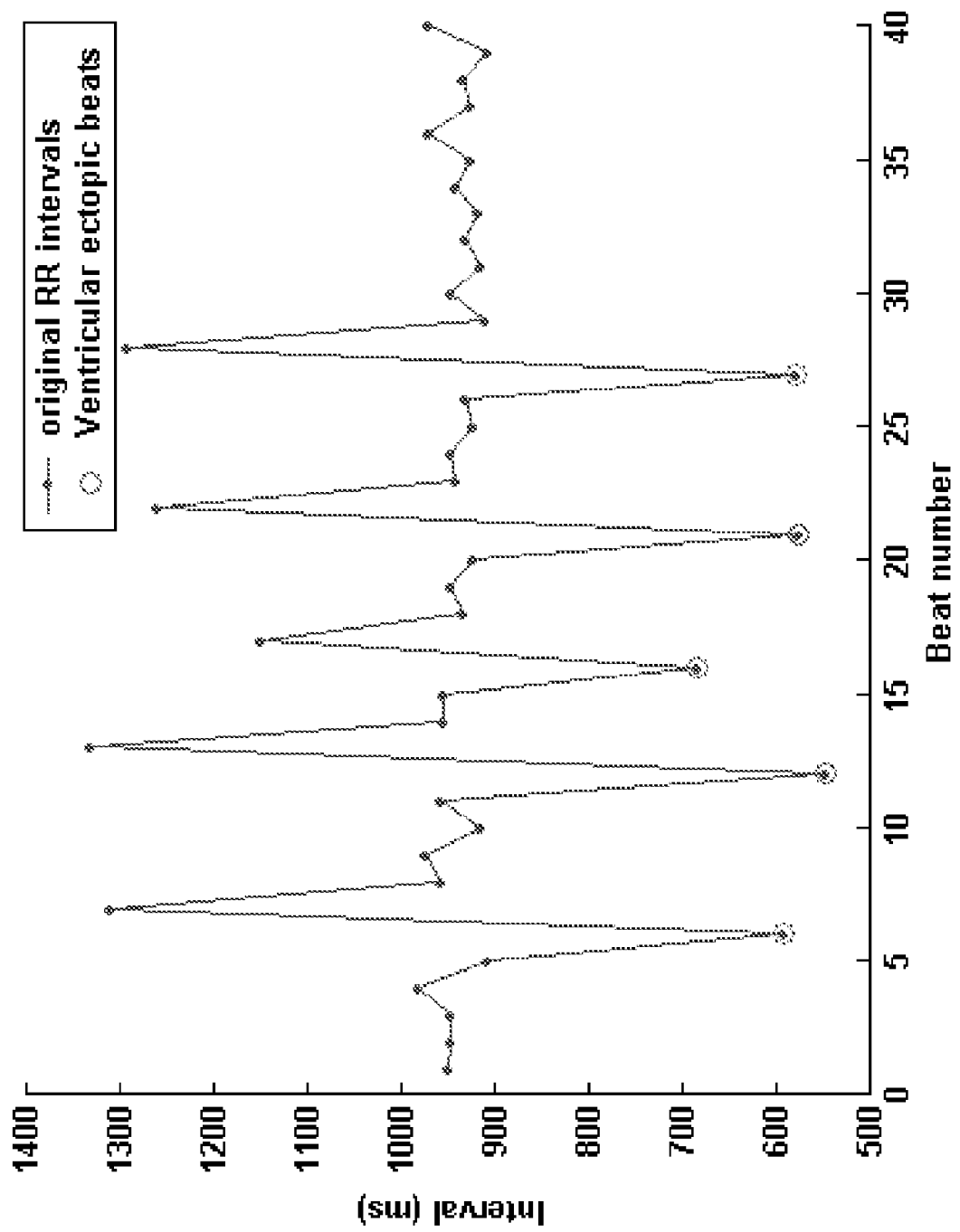
FIG. 16 shows the original RR intervals shown in FIG. 9, and the results of Ectopic Beat detection.

FIG. 16 shows the original 40 RR intervals and the results of Ectopic Beat detection (ventricular Ectopic Beats are marked by circles), by applying the morphological filters to the RR intervals, and using the detection criteria shown in FIG. 6.

Figure 17:
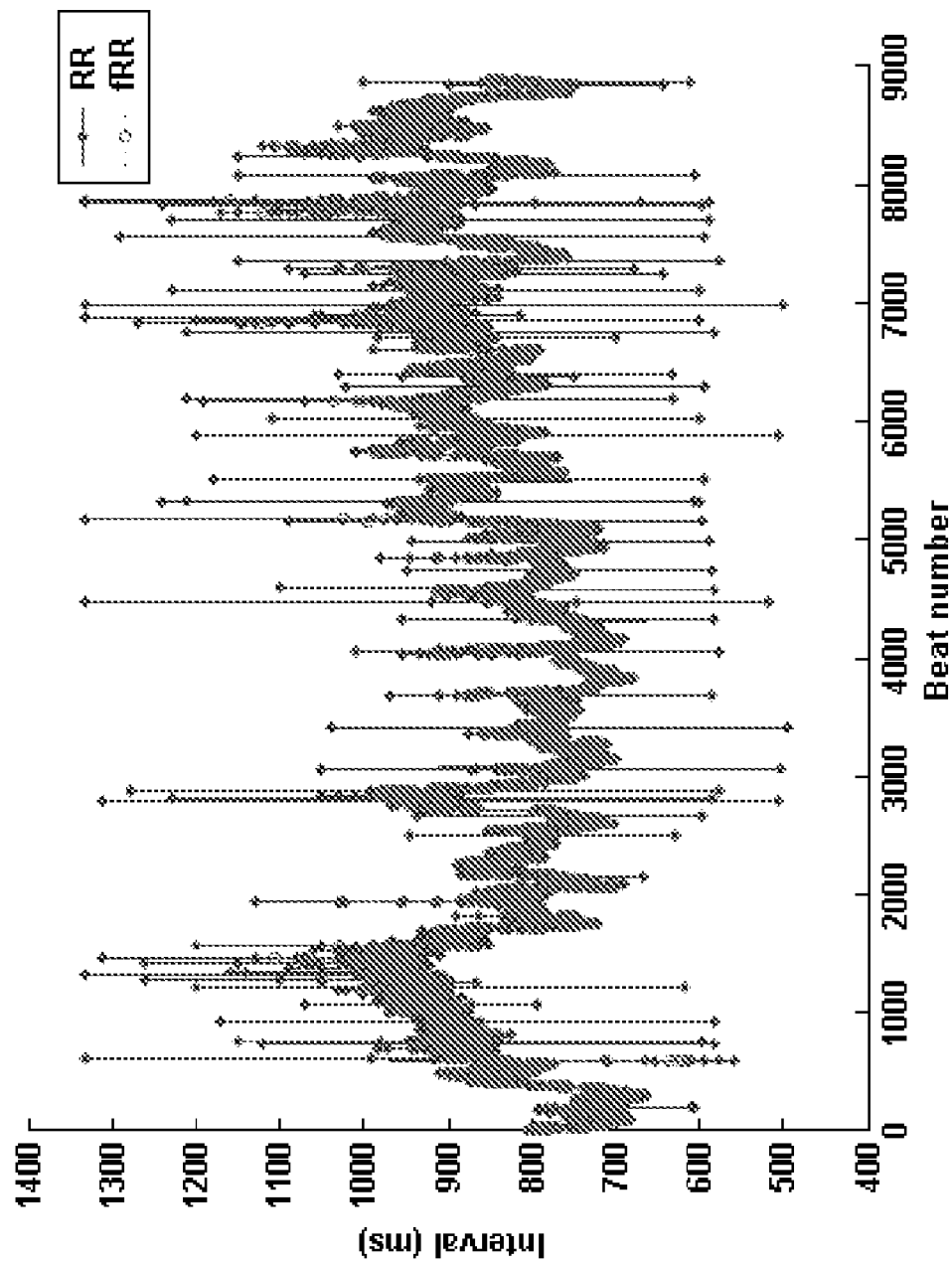
FIG. 17 shows another example of a long episode of RR intervals, together the filtered fRR intervals after applying the morphological filter shown in FIG. 5.
Figure 18:
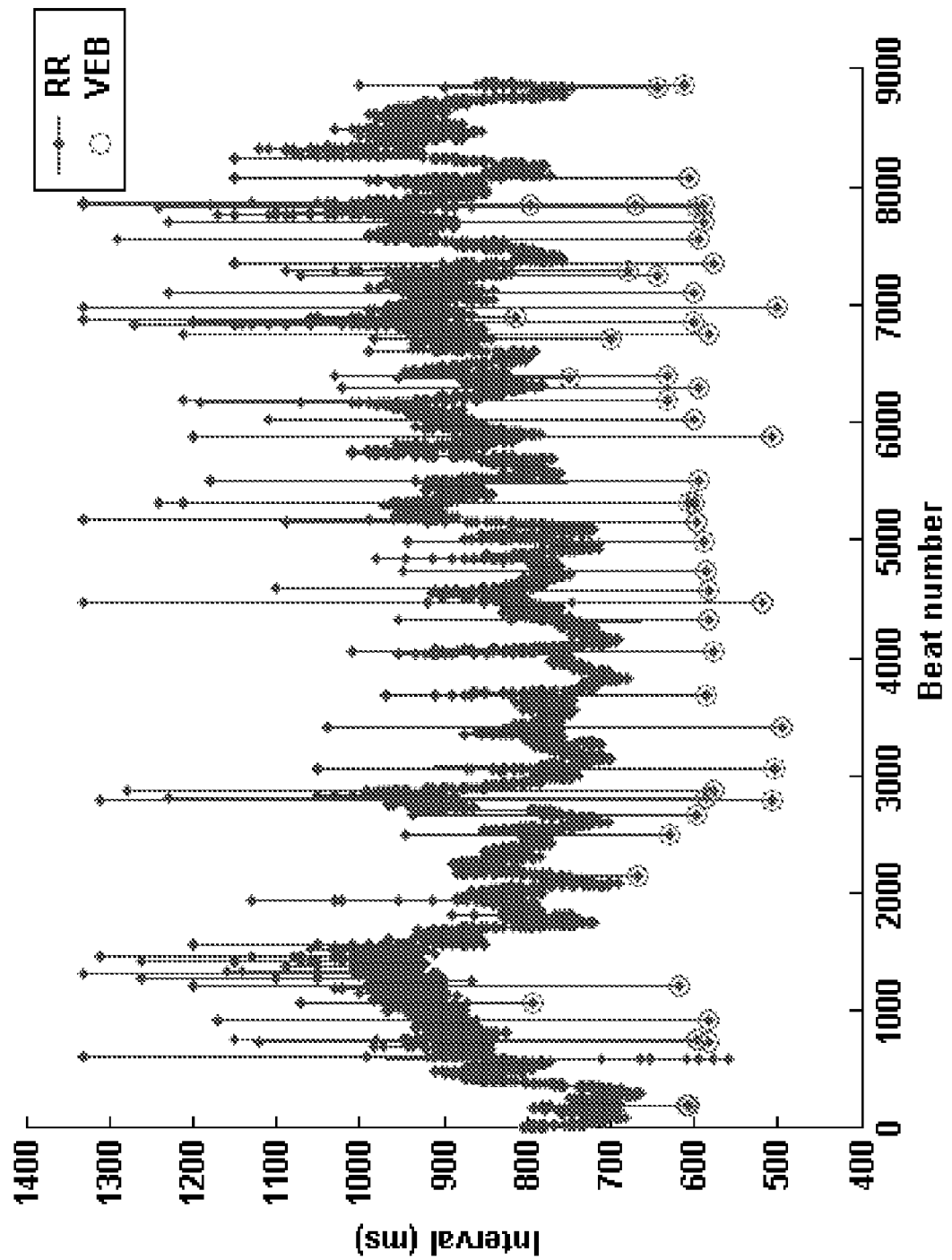
FIG. 18 shows the original RR intervals shown in FIG. 17, and with the results of Ectopic Beat detection.

FIG. 17 shows another example of a long episode of tachogram that consists of over 8000 RR intervals, as well as the filtered RR intervals (fRR) after applying the morphological filter shown in FIG. 5 to remove the impulse RR intervals. The original RR intervals are further plotted in FIG. 18, together with the results of Ectopic Beat detection (ventricular Ectopic Beats are marked by circles), after applying the morphological filters to the RR intervals, and using the detection criteria shown in FIG. 6.

Figure 19:
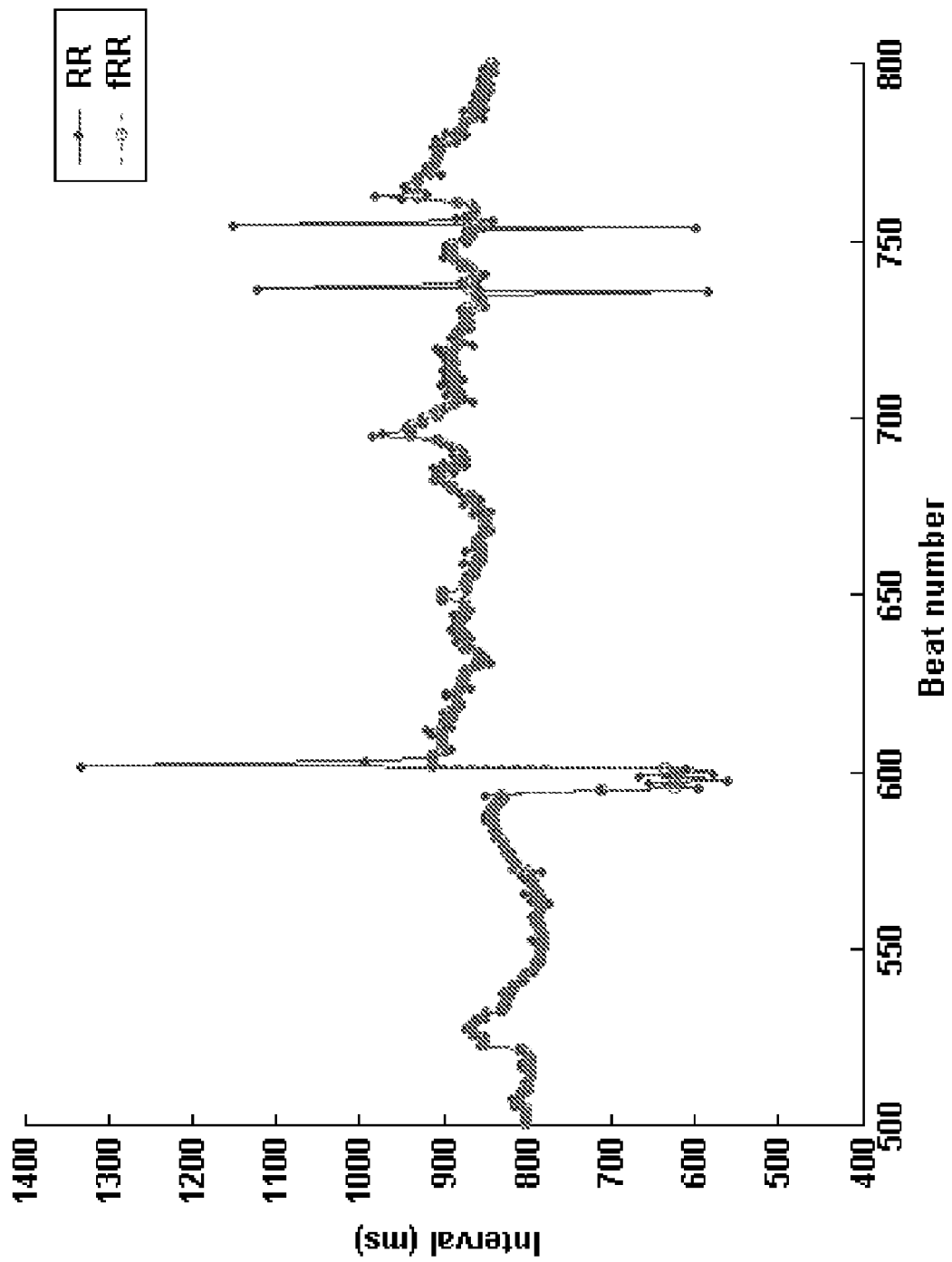
FIG. 19 shows a zoomed view of FIG. 17 that includes a segment of RR intervals and the corresponding filtered fRR intervals.
Figure 20:
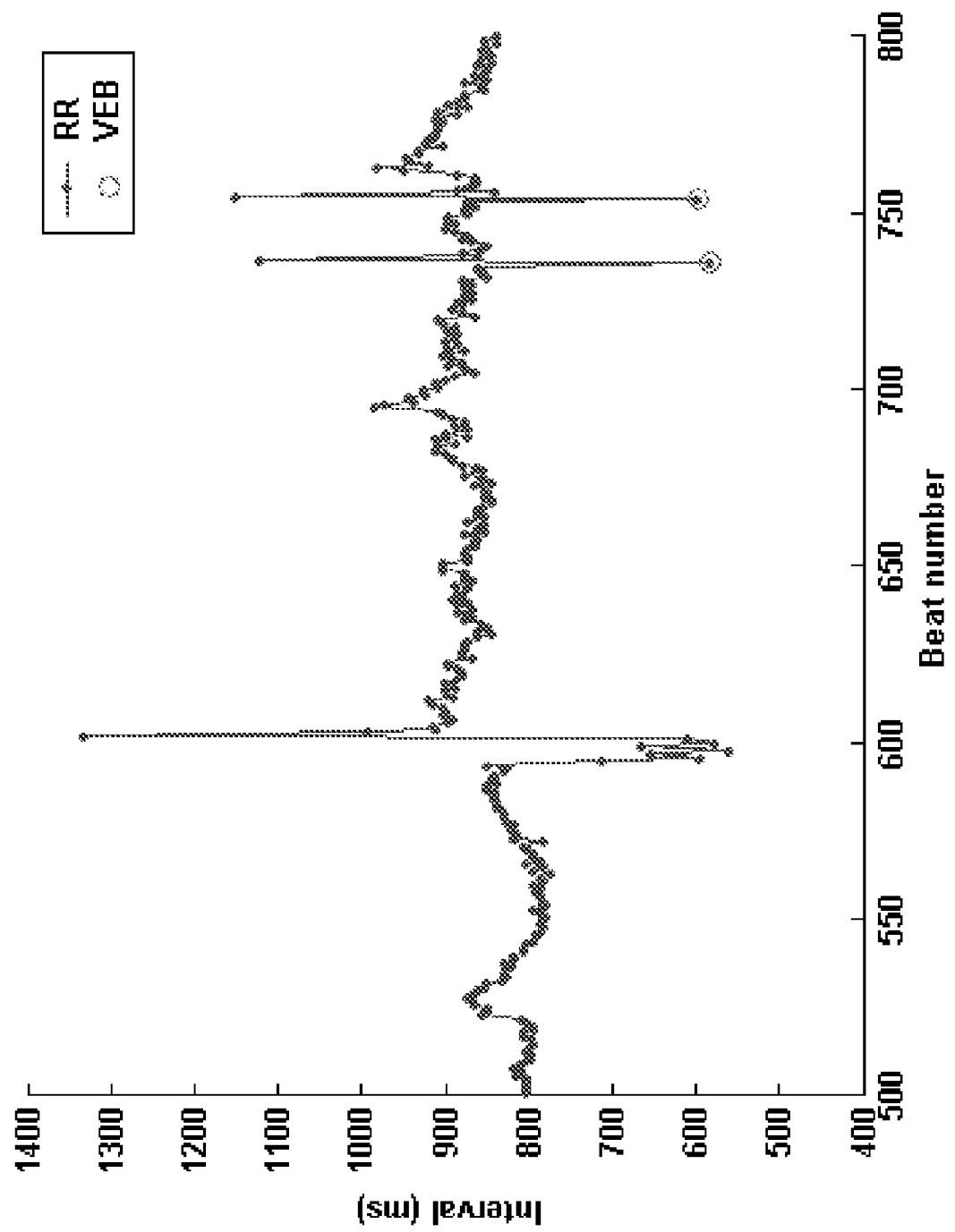
FIG. 20 shows a zoomed view of FIG. 18 that includes a segment of RR intervals and the Ectopic Beat detection results.

FIG. 19 shows a zoomed view of FIG. 17 that includes a segment of 300 RR intervals and the corresponding filtered fRR intervals. Note that there are 7 consecutive short RR intervals that are not removed by the impulse filter. FIG. 20 shows a zoomed view of FIG. 18 that includes the same segment of 300 RR intervals and the Ectopic Beat detection results. Evidently, these 7 consecutive short RR intervals are not detected as ventricular Ectopic Beats.

Figure 21:
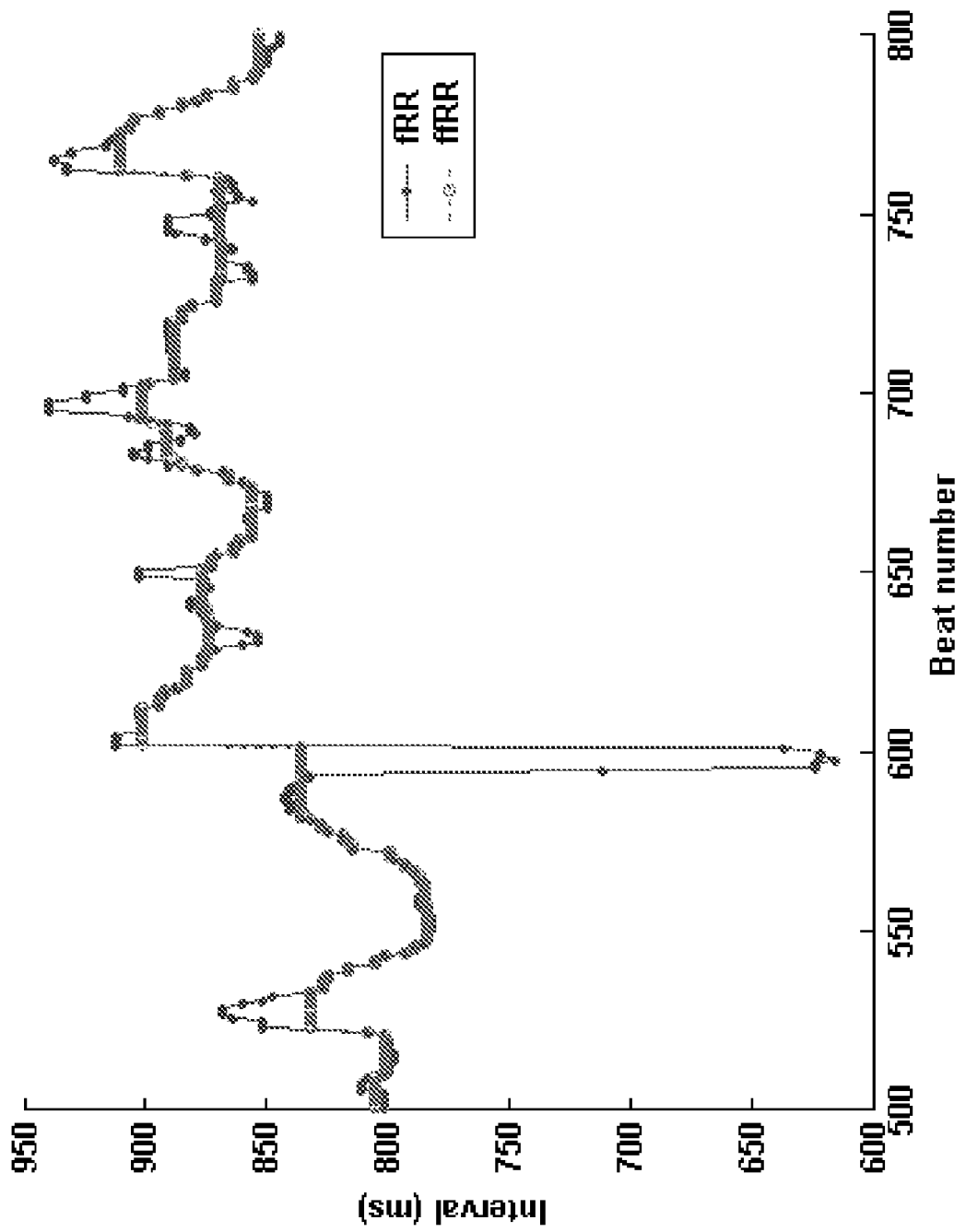
FIG. 21 shows the initially filtered fRR intervals shown in FIG. 19, together with the further filtered intervals ffRR.
Figure 22:
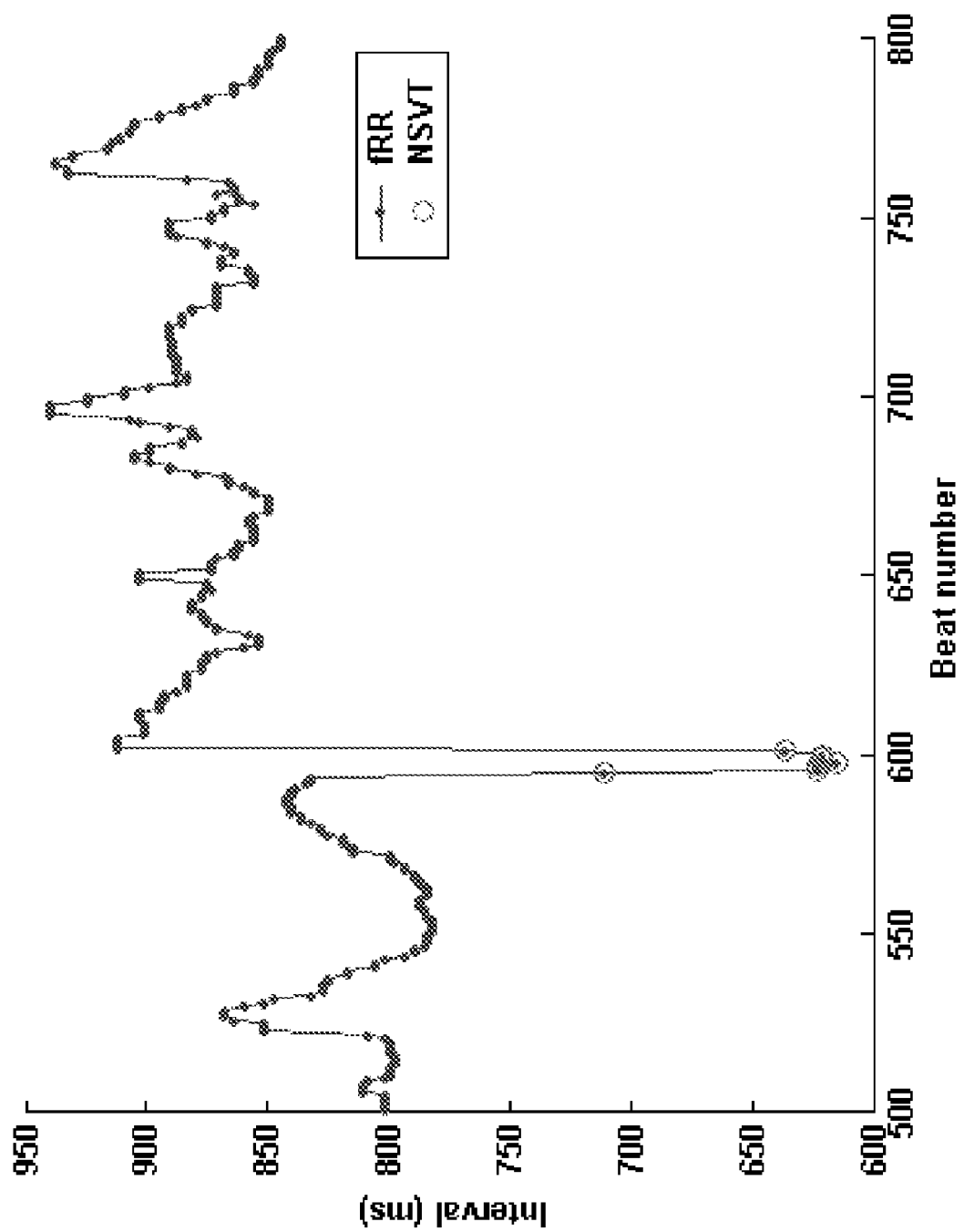
FIG. 22 shows the initially filtered fRR intervals, together with the NSVT detection results.

As illustrated in FIG. 7, the initially filtered fRR intervals (free of impulse RR intervals) can be further processed by a second morphological impulse filter to detect multiple consecutive abnormal RR intervals. FIG. 21 shows the initially filtered 300 fRR intervals shown in FIG. 19, together with the further filtered intervals ffRR (note the second morphological impulse filter uses an 11-zero SE in this example). Clearly, the 7 consecutive short RR intervals are removed in the ffRR intervals. The initially filtered 300 fRR intervals are further plotted in FIG. 22, together with the NSVT detection results (marked by circles) using the detection criteria shown in FIG. 8. Clearly, the 7 consecutive short RR intervals are corrected detected as an episode of NSVT.

As illustrated in the above examples, using morphological filters can effectively remove the impulse RR intervals to get the trend of RR intervals, and detect the abnormal cardiac intervals, including but are not limited to Ectopic Beats, episode of NSVT, sudden RR pauses, etc. These morphological operators are particularly suitable for application in low-power devices such as the subcutaneous ECG monitor as exemplified in this invention, because of their very high computation efficiency, and feasibility for implementation in hardware platform.

While the above descriptions use subcutaneous ECG as an example to illustrate the concept of morphological filtering of RR intervals, it is also obvious to the people who are skilled in the art to apply the same concept and method to general time series analysis of cardiac intervals, e.g., to detect and remove abnormal cardiac beats based on RR intervals measured from a plural of biological signals, including but are not limited to, the surface ECG signal, the IEGM signal, the blood pressure signal, the transthoracic impedance signal, the pulse oximeter signal, finger plethysmography signal, etc.

Furthermore, it is also obvious to the people skilled in the art to apply the same concept and method for abnormal beat detection and removal based on time series analysis of various metrics (other than the RR intervals) that are derived from the biological signal, such as surface ECG, subcutaneous ECG, IEGM, blood pressure, etc. For instance, it is well known that the QRS morphology of a ventricular Ectopic Beat is usually different than that of a normal conducted beat. Such morphological difference can be quantified by means of a plural of metrics, including but are not limited to, the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex, and so on. Therefore, abnormal beat detection and removal can also be achieved by applying the morphological filters to the time series of these derived metrics.

It is further understood that abnormal beat detection and removal can also be achieved by applying morphological filters independently to two or more physiological signals. For example, one set of morphological filters are applied to the measured RR intervals, and another set of morphological filters are applied to the time series of a derived metric (e.g., QRS width). The morphological filtering of multiple physiological signals run in parallel, and each branch performs independent impulse (RR interval or derived metric) detection and removal. The results from these multiple branches are then pooled together for final detection and removal of the abnormal cardiac cycles. In one typical embodiment, a beat is classified as an abnormal beat if all branches of the morphological filtering classify the beat as an abnormal beat. In another typical embodiment, a beat is classified as an abnormal beat if any branch of the morphological filtering classifies the beat as an abnormal beat. Obviously other logical operations can be similarly implemented.

Although an exemplary embodiment of the present invention has been shown and described, it should be apparent to those of ordinary skill that a number of changes and modifications to the invention may be made without departing from the spirit and scope of the invention. All such changes, modifications and alterations should therefore be recognized as falling within the scope of the present invention.

What is claimed is:

1. A heart monitor for detecting ectopic beats in an electrocardiogram signal comprising:
   an implantable device configured to monitor an electrocardiogram signal subcutaneously;
   an electrocardiogram signal input coupled with said implantable device and configured to obtain said electrocardiogram signal;
   a first signal analyzer connected to said electrocardiogram signal input, said first signal analyzer configured to generate a first time series of values that represent each duration of a respective measured RR interval derived from said electrocardiogram signal;
   a second signal analyzer configured to generate a modified time series of values that represent a trend of values of said first time series through application of one or more morphological operators comprising an erosion operator or a dilation operator or any combination thereof and to remove abnormal RR intervals from said first time series of values that represent each duration of the respective measured RR-interval, to thus derive the modified time series of RR-intervals that represent a trend of RR intervals; and,
   a comparison stage configured to compare said first time series with said modified time series and thus
     detect ectopic beats from said modified time series generated with a first discrete kernel function of a first length or
     detect non-sustained ventricular tachycardia from said modified time series generated with a second discrete kernel function of a second length wherein said second length is greater than said first length or
     detect both ectopic beats from said modified time series generated with said first discrete kernel function of said first length and non-sustained ventricular tachycardia from said modified time series generated with said second discrete kernel function of said second length wherein said second length is greater than said first length.

2. The heart monitor of claim 1,
   wherein said first signal analyzer is further configured to generate a QRS metrics time series of values that represent QRS metrics, wherein each value of said time series represents at least one of the QRS metrics, comprising
     a width of a QRS complex, or
     a positive or negative peak amplitude of the QRS complex, or
     an absolute area under the QRS complex, or
     maximum positive or negative slopes of the QRS complex, or
     a dominant frequency component of the QRS complex, or
     complexity measures of the QRS complex; and,
   wherein said second signal analyzer is configured to further apply said one or more morphological operators comprising said erosion operator or said dilation operator or said any combination thereof to the QRS metrics time series of values that represent said QRS metrics and to remove abnormal QRS metrics from said QRS metrics time series of values that represent said QRS metrics to thus derive another modified time series that represent a trend of said QRS metrics and use said trend of QRS metrics in combination with said modified time series in said comparison stage if at least one or both of said trend of QRS metrics and said modified time series classify a beat as abnormal.

3. The heart monitor of claim 2 wherein said comparison stage is configured to subtract said first time series from said modified time series and to thus generate difference signal values and detect said abnormal RR intervals or the QRS metrics through comparison of said difference signal values to at least one threshold value.

4. The heart monitor of claim 2 wherein said comparison stage is configured to generate a series of ratio values through division of each value of said first time series by an associated value of said modified time series and to compare each ratio value thus derived with at least one threshold value.

5. The heart monitor of claim 3 wherein said comparison stage is configured to generate both the difference signal values and configured to generate a series of ratio values through division of each value of said first time series by an associated value of said modified time series and to compare each difference signal value to at least one threshold value and to compare each ratio value with another at least one threshold value.

6. The heart monitor of claim 1 wherein said the second signal analyzer is configured to generate said modified time series through application of both an opening operator and a closing operator to said first time series to thus obtain said modified time series of values that represent the trend of values of said first time series.

7. The heart monitor of claim 6, wherein said the second signal analyzer is configured to generate said modified time series by applying said erosion operator followed by said dilation operator that together form the opening operator to suppress peaks in the first time series.

8. The heart monitor of claim 6 wherein the second signal analyzer is configured to generate said modified time series by applying said dilation operator followed by said erosion operator that together form the closing operator to suppress pits in the first time series.

9. The heart monitor of claim 1 further comprising a third signal analyzer that is configured to detect multiple cycles of consecutive short RR intervals or multiple cycles of consecutive long RR intervals or both to detect said non-sustained ventricular tachycardia.

10. The heart monitor of claim 1 wherein said first discrete kernel function of said first length is filled with zeros or wherein said second discrete kernel function of said second length is filled with zeros or wherein said first and said second discrete kernel functions are both filled with zeros to avoid a subtraction operation.

11. A method for detecting ectopic beats in an electrocardiogram signal comprising:

obtaining an electrocardiogram signal with an implantable device that is monitoring an electrocardiogram signal subcutaneously with an electrocardiogram signal input;

generating from said electrocardiogram signal a first time series of values that represent each duration of a respective measured RR interval derived from said input electrocardiogram signal via a first signal analyzer;

generating a modified time series of values that represent a trend of values of said first time series by applying one or more morphological operators comprising an erosion operator or a dilation operator or any combination thereof and to remove abnormal RR intervals from said first time series of values that represent each duration of the respective measured RR-interval, to thus derive the modified time series of RR-intervals that represent a trend of RR intervals via a second signal analyzer; and, comparing said first time series with said modified time series via a comparison stage and thus detecting ectopic beats from said modified time series generated with a first discrete kernel function of a first length or detecting non-sustained ventricular tachycardia from said modified time series generated with a second discrete kernel function of a second length wherein said second length is greater than said first length or detecting both ectopic beats from said modified time series generated with said first discrete kernel function of said first length and non-sustained ventricular tachycardia from said modified time series generated with said second discrete kernel function of said second length wherein said second length is greater than said first length.

12. The method of claim 11, further comprising generating from said electrocardiogram signal a QRS metrics time series comprises generating a time series of values that represent QRS metrics from said first time series, wherein each value of said time series represents at least one of the QRS metrics, comprising a width of a QRS complex, or a positive or negative peak amplitude of the QRS complex, or an absolute area under the QRS complex, or maximum positive or negative slopes of the QRS complex, or a dominant frequency component of the QRS complex, or complexity measures of the QRS complex; and, wherein said generating said modified time series comprises further applying said one or more morphological operators comprising said erosion operator or said dilation operator or said any combination thereof to the QRS metrics time series of values that represent said QRS metrics and removing abnormal QRS metrics from said first time series of values that represent QRS metrics and thus deriving another modified time series that represent a trend of said QRS metrics and using said trend of QRS metrics in combination with said modified time series in said comparison stage if at least one or both of said trend of QRS metrics and said modified time series classify a beat as abnormal.

13. The method of claim 12 wherein said comparing said first time series with said modified time series comprises subtracting said first time series from said modified time series to thus generate difference signal values and detecting abnormal RR intervals or QRS metrics by comparing said difference signal values to at least one threshold value.

14. The method of claim 12 wherein said comparing said first time series with said modified time series comprises generating a series of ratio values by dividing each value of said first time series by an associated value of said modified time series and comparing each ratio value thus derived with at least one threshold value.

15. The method of claim 13 wherein said comparing said first time series with said modified time series comprises generating both said difference signal values and wherein said comparing said first time series with said modified time series further comprises generating a series of ratio values by dividing each value of said first time series by an associated value of said modified time series and comparing each difference signal value to at least one threshold value and comparing each ratio value with another at least one threshold value.

16. The method of claim 11 wherein said step of generating said modified time series comprises applying both, an opening operator and a closing operator to said first time series to thus obtain said modified time series of values that represent the trend of values of said first time series.

17. The method of claim 16, wherein said generating said modified time series comprises applying said erosion operator followed by said dilation operator that together form the opening operator to suppress peaks in said first time series and/or wherein said generating said modified time series comprises applying said dilation operator followed by said erosion operator that together form the closing operator to suppress pits in the first time series.

18. The method of claim 17 further comprising processing the trend of values of the first time series to detect multiple cycles of consecutive short RR intervals or multiple cycles of consecutive long RR intervals or both and detecting said non-sustained ventricular tachycardia.

19. The method of claim 11 further comprising using said first discrete kernel function of said first length filled with zeros or using said second discrete kernel function of said second length filled with zeros or using said first and said second discrete kernel functions both filled with zeros to avoid a subtracting operation.

\* \* \* \* \*